United States Patent
Falk

(10) Patent No.: US 9,687,380 B1
(45) Date of Patent: Jun. 27, 2017

(54) CERVICAL COLLAR BRACE KIT, COLLAR BLANKS, METHODS OF FORMING A MODEL OF A PATIENT, AND METHODS OF FORMING COLLAR BLANKS

(71) Applicant: David L. Falk, Lantana, FL (US)

(72) Inventor: David L. Falk, Lantana, FL (US)

( * ) Notice: Subject to any disclaimer, the term of this patent is extended or adjusted under 35 U.S.C. 154(b) by 307 days.

(21) Appl. No.: 14/338,806

(22) Filed: Jul. 23, 2014

Related U.S. Application Data

(60) Provisional application No. 61/996,625, filed on May 12, 2014.

(51) Int. Cl.
 *A61F 5/00* (2006.01)
 *A61F 5/055* (2006.01)

(52) U.S. Cl.
 CPC .................................... *A61F 5/055* (2013.01)

(58) Field of Classification Search
 CPC .. A61F 13/12; A61F 5/01; A61F 5/055; A61F 5/058
 USPC .......................................................... 602/18
 See application file for complete search history.

(56) References Cited

U.S. PATENT DOCUMENTS

| | | |
|---|---|---|
| 2,801,630 A | 8/1957 | Moore |
| 2,818,063 A | 12/1957 | Smith et al. |
| 2,911,970 A | 11/1959 | Bartels |
| 3,024,784 A | 3/1962 | Monfardini |
| 3,042,026 A | 7/1962 | Monfardini |
| 3,055,358 A | 9/1962 | Di Palma et al. |
| 3,135,256 A | 6/1964 | Gruber |
| 3,189,026 A | 6/1965 | Barnett |
| 3,285,243 A | 11/1966 | Yellin |
| 3,285,244 A | 11/1966 | Cottrell |
| 3,374,785 A | 3/1968 | Gaylor, Jr. |
| 3,756,226 A | 9/1973 | Calabrese et al. |
| 3,850,164 A | 11/1974 | Hare |
| 3,916,885 A | 11/1975 | Gaylord, Jr. |
| 4,043,325 A | 8/1977 | Ochs et al. |
| 4,520,801 A | 6/1985 | Lerman |
| 4,538,597 A | 9/1985 | Lerman |
| 4,955,368 A | 9/1990 | Heimann |

(Continued)

FOREIGN PATENT DOCUMENTS

| | | | |
|---|---|---|---|
| CN | 202436648 U | * | 9/2012 |
| DE | 3318938 A1 | | 11/1984 |

(Continued)

*Primary Examiner* — Kim M Lewis
(74) *Attorney, Agent, or Firm* — Womble Carlyle Sandridge & Rice, LLP

(57) ABSTRACT

A kit for modeling a patient's neck area and creating a neck brace that is sized specifically for an individual patient. Combinations of components are chosen to build the model according to the actual measurements of the patient. A front and back blank are molded to correspond to the model, typically by heat molding. Once cooled, the blanks are removed from the model and Velcro®, padding, and a Velcro® strap are added to form a custom cervical collar brace. The front and back blanks can be formed on preformed blank molds, or can involve a method of forming blank molds upon which front or back blanks or both can be formed. The method can involve applying a material, such as low density polyethylene, to the blank mold and conforming the material to the mold. The blank can then be cut from the material, typically along an outline or contours.

26 Claims, 40 Drawing Sheets

(56) References Cited

U.S. PATENT DOCUMENTS

| | | |
|---|---|---|
| 4,969,453 A | 11/1990 | Heimann |
| 4,987,891 A | 1/1991 | Gaylord, Jr. et al. |
| 5,005,564 A | 4/1991 | Grundei et al. |
| 5,058,572 A | 10/1991 | Schmid et al. |
| 5,060,637 A | 10/1991 | Schmid et al. |
| 5,520,619 A | 5/1996 | Martin |
| 5,728,054 A | 3/1998 | Martin |
| 5,795,315 A | 8/1998 | Traut et al. |
| 5,993,403 A | 11/1999 | Martin |
| 6,036,664 A | 3/2000 | Martin, Sr. et al. |
| 6,090,058 A | 7/2000 | Traut et al. |
| 6,245,033 B1 | 6/2001 | Martin |
| 6,726,643 B1 | 4/2004 | Martin |
| 7,041,073 B1 | 5/2006 | Patron |
| 7,399,288 B2 | 7/2008 | Chao |
| 7,674,234 B2 | 3/2010 | Calco et al. |
| 8,038,636 B2 | 10/2011 | Thorgilsdottir et al. |
| 8,491,512 B2 | 7/2013 | Donaldson et al. |
| 8,545,423 B2 | 10/2013 | Patron |
| 8,740,830 B2 | 6/2014 | Suarez et al. |
| 2012/0101417 A1* | 4/2012 | Joseph ..................... A61F 5/01 602/5 |
| 2012/0130295 A1 | 5/2012 | Haider |
| 2014/0180185 A1* | 6/2014 | Zachariasen ............. A61F 5/01 602/5 |

FOREIGN PATENT DOCUMENTS

| | | |
|---|---|---|
| WO | WO 00/49979 A1 | 8/2000 |
| WO | WO 2011/019379 A1 | 2/2011 |

\* cited by examiner

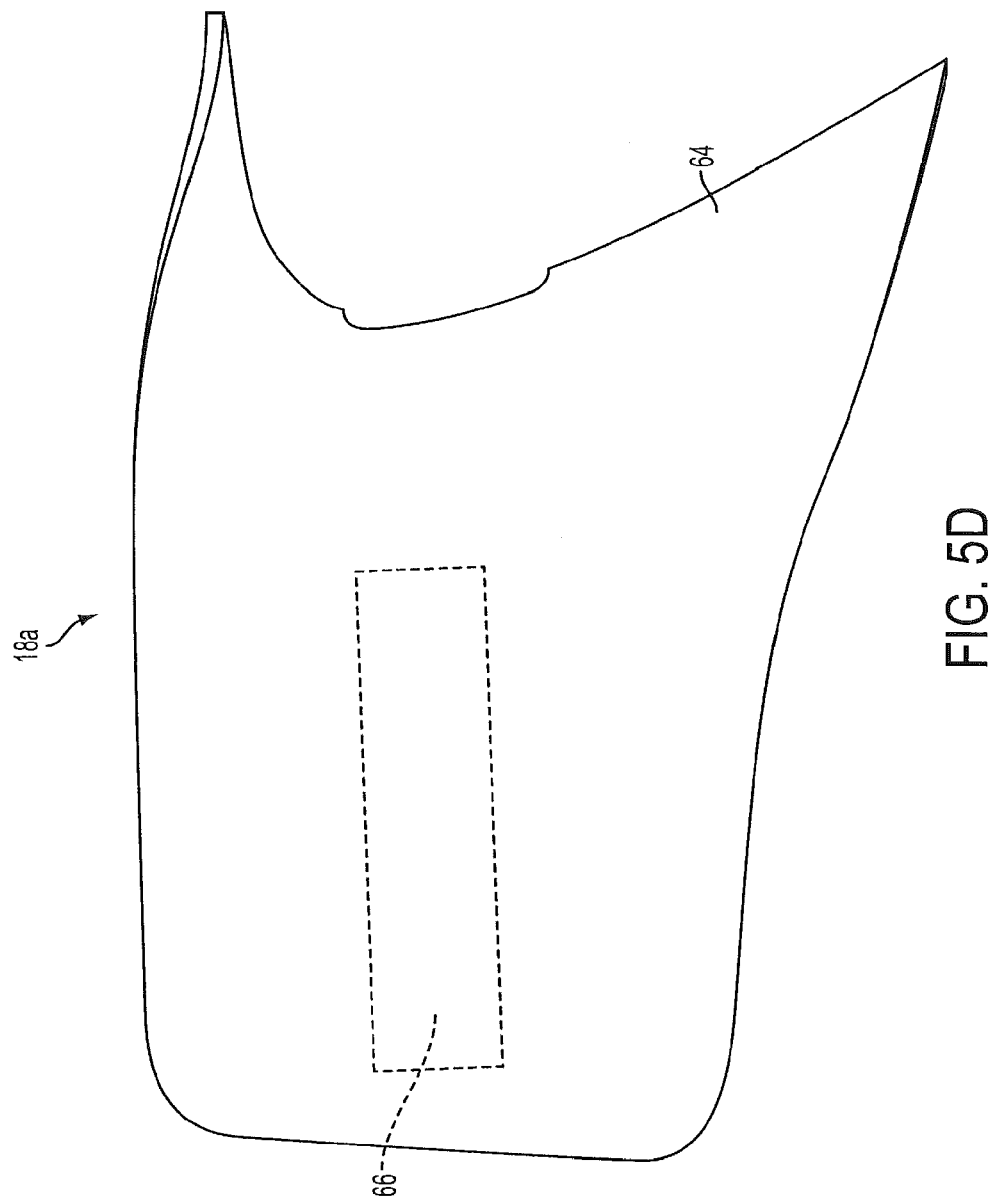

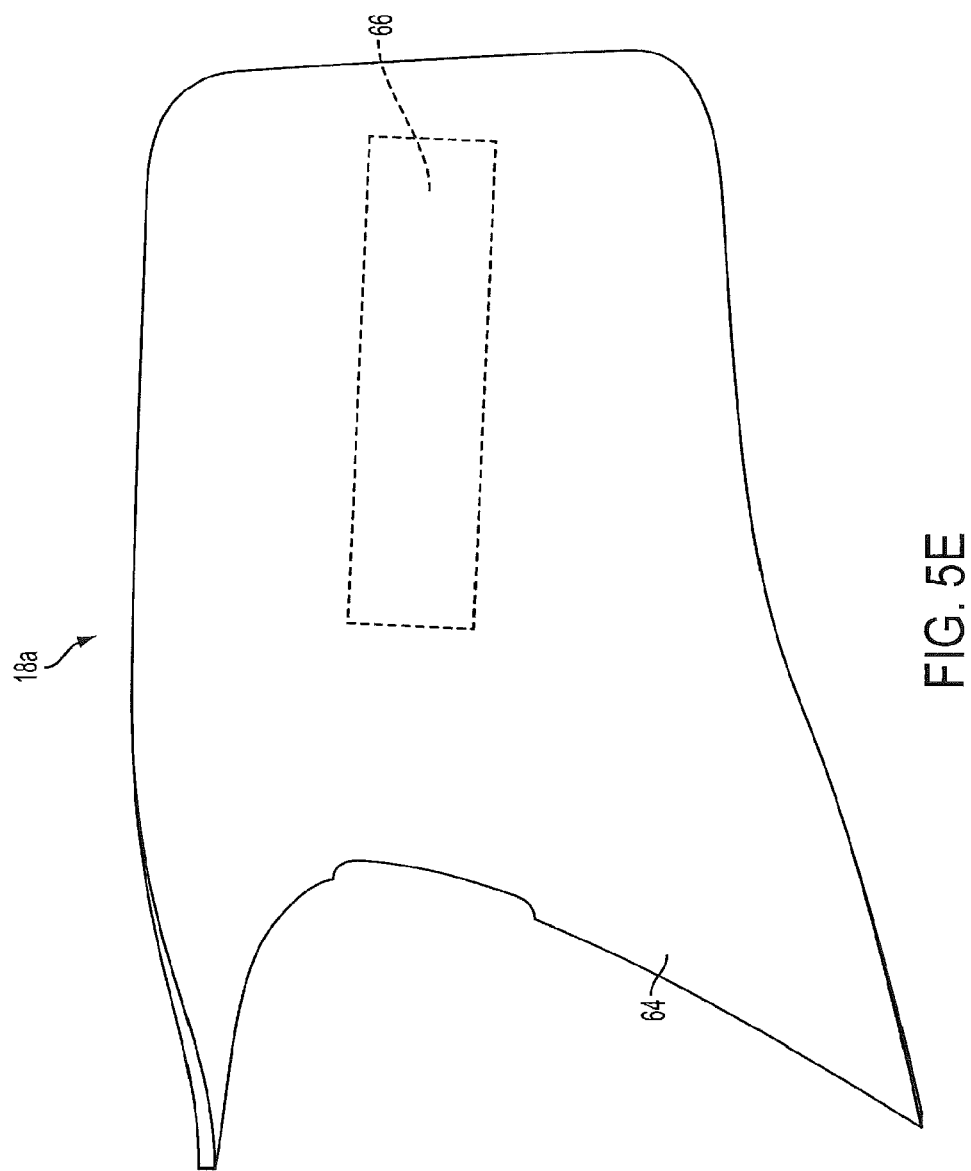

CERVICAL COLLAR BRACE KIT, COLLAR BLANKS, METHODS OF FORMING A MODEL OF A PATIENT, AND METHODS OF FORMING COLLAR BLANKS

CROSS-REFERENCE TO RELATED APPLICATION

The present application is a formalization of previously filed, U.S. Provisional Patent Application Ser. No. 61/996,625, filed May 12, 2014 by the inventor named in the present application. This application claims the benefit of the filing date of the cited Provisional Patent Application according to the statutes and rules governing provisional patent applications, particularly 35 U.S.C. §119(a)(i) and 37 C.F.R. §1.78(a)(4) and (a)(5). The specification and drawings of the Provisional Patent Application referenced above are specifically incorporated herein by reference as if set forth in their entirety.

FIELD OF DISCLOSURE

The present disclosure generally relates to a collar brace kit and a blank, and more specifically, to a custom fabricated collar brace and method to make the same.

SUMMARY OF DISCLOSURE

In one aspect, the present invention includes an embodiment that generally relates to measuring a patient's neck area, creating a model mimicking the measurements of the patient, and creating a neck brace from the model that is sized specifically for the individual patient. Generally, in order to form the individual's personal brace, the patient's neck area is first measured, including, for example, the neck circumference, distance of the chin to the sternal notch, distance of earlobe to top of the shoulder, and various other measurements. A combination of appropriate size model components is chosen to form the model for the individual patient according to the actual patient measurement taken.

Generally, in one aspect, the model components are selected from neck blocks and can include selecting a chin and occipital base section and a chest base section. Next, the model is built based on the appropriate sized model components, with a larger sized patient requiring use of larger sized model components, while a smaller sized patient requiring use of smaller sized model components. In an alternative embodiment, an expandable bladder apparatus can be used in place of the neck blocks, with the expandable bladder apparatus capable of being sized to mimic a patient's measurements. Once the model is completed to mimic an individual patient, a front model blank and a back model blank are each molded to correspond to the model of the individual patient. The front blank and back blank molding is performed, typically by heat molding the front blank (and then separately the back blank) with a heating device to "fit" onto the model. Once the blanks are molded with heat, the blanks are allowed to cool. The blanks are then removed from the model and Velcro®, padding, and/or a Velcro® strap are added to form a custom cervical collar brace. The collar brace can then be trimmed (i.e., as required, the front blank, back blank, padding, or Velcro®) when fitted onto the patient if required to achieve a better fit.

In one aspect, a kit for making a custom configured neck brace can comprise a model having a selectively configurable neck portion and at least one blank having an initial configuration, with the blank being formed of a material that is malleable when heated to a predetermined temperature. The initial configuration of the blank allowing the blank to be placed onto at least the neck portion of the model. The blank being transformable to a final configuration different from the initial configuration when the blank is placed onto at least the neck portion of the model and heated, thereby forming at least a part of the custom configured neck brace. The neck portion of the kit can further comprise neck blocks, with the neck portion having a neck portion height and a neck portion width and with the neck blocks including at least a first neck block having a first neck block height and a first neck block width. The neck portion height can be increased by adding at least a second neck block of the neck blocks, with the second neck block having a second neck block height and a second neck block width. The first neck block width and the second neck block width can be equal, or the second neck block height can be different than the first neck block height. Additionally, the neck portion height can be increased by adding at least a third neck block of the neck blocks and can be decreased by removing either the first neck block, the second neck block, or the third neck block. The third neck block can have a third neck block height, with the third neck block height being different than either the first neck block height, the second neck block height, or both the first neck block height and the second neck block height. The model can further comprise a head portion and an upper chest portion, with the initial configuration of the blank allowing the blank to be placed onto at least a portion of the head portion, the neck portion, and the upper chest portion.

In one aspect, the kit can optionally further comprise at least one chest base having a base portion, a front portion connected to the base portion, and a back portion connected to the base portion. Each of the front portion and the back portion can be configured to increase the size of the upper chest portion of the model to mimic a user and at least one chin and occipital base having a base portion, an occipital portion connected to the base portion, and a chin portion connected to the base portion. Each of the occipital portion and the chin portion can be configured to increase the size of a chin and occipital portion of the model to mimic the user. The head portion, the neck portion, and the upper chest portion can be removably securely attached to one another by one of the following: Velcro®, tongue and groove attachment, snaps, or at least one channel that extends from the top of the head portion through the neck portion and to the bottom of the upper chest portion. If the head portion, the neck portion, and the upper chest portion are attached with at least one channel, the at least one channel being configured to receive at least one rod to secure the head portion, neck portion, and upper chest portion together. The at least one rod either corresponds to the number of channels or is less than the number of channels. The kit can further comprise one or more of the following: measurement tools, a collar measurement form, a heating device for heating the at least one blank, and a wrap for holding the at least one blank to the model.

Additionally, in one aspect, the blank formed can either be a front blank or a back blank, and the kit can further comprise a securing strap for securing the front blank and the back blank together. Further, the securing strap can have hook and loop fasteners. Also, the kit can further comprise a pad kit with foam padding attachable to the front blank or the back blank, and hook and loop fasteners for attaching the foam padding to the front blank or the back blank. The kit can also further comprise at least one wedge shaped neck block and at least one flexed rod to accommodate for uncorrectable flexion of the neck.

In one aspect, a method for making a custom configured neck brace can comprise the steps of: obtaining a neck circumference and a chin to sternal notch distance of a user, selecting neck blocks that correspond generally to the chin to sternal notch distance and to the neck circumference, with the selected neck blocks forming a neck portion, attaching the neck portion to a chin portion and an upper chest portion to create a model, obtaining at least one blank having an initial configuration, with the at least one blank being formed of a material that is malleable when heated to a predetermined temperature, placing the at least one blank onto at least the neck portion of the model, heating the at least one blank to at least the predetermined temperature, allowing the at least one blank to transform to a final configuration different from the initial configuration, allowing the at least one blank to cool in the final configuration, and removing the at least one blank from the model. The head portion, the neck portion, and the upper chest portion can be removably securely attached to one another by one of the following: Velcro®, tongue and groove attachment, snaps, or at least one channel that extends from the top of the head portion through the neck portion and to the bottom of the upper chest portion. The at least one channel can be configured to receive at least one rod to secure the head portion, neck portion, and upper chest portion together. The at least one rod either can correspond to the number of channels or can be less than the number of channels. The method can further comprise securing the head portion, the neck portion, and the upper chest portion together to form the model. The obtaining of the neck circumference and the chin to sternal notch distance can comprise measuring the neck circumference and the chin to sternal notch distance of a user. The measuring can further comprise the steps of: measuring a distance of the occiput to a spinous process of C7 vertebra of the user, measuring a distance from the bottom of the earlobe to a highest part of a shoulder of the user, measuring a distance of the neck anterior to the neck posterior of the user, and measuring a distance of the neck medial to the neck lateral of the user. The at least one rod can be a flexed rod and the neck blocks can be wedge shaped neck blocks. The method can further comprise, after heating, wrapping the at least one blank with a wrap to hold the at least one blank in place against the model during cooling, and, after removing, applying padding to the final configuration.

In one aspect, the at least one blank in the method can comprise a front blank for molding the front of the model or a back blank for molding the back of the model. Optionally, padding can be added to the front blank or the back blank. Additionally, the method can be repeated to form both a front blank and a back blank to be used in combination by securing the front blank to the back blank with a fastener.

In one aspect, a blank for forming a neck brace can comprise an initial configuration allowing the blank to be placed onto a model having at least a neck portion and a material that is malleable when heated to a predetermined temperature. The blank can be capable of transforming to a final configuration different from the initial configuration that conforms generally to the shape of the at least the neck portion of the model when heated.

In one aspect, the blank can further comprise an interior surface and an exterior surface and can have a central portion, an upper portion, and a lower portion, with the upper portion and the lower portion extend outwardly from the central portion. The central portion of the interior surface can define a substantially parabolic shaped interior space and the exterior surface can have a generally concave shape.

Further, the blank can be formed of a material that is a low density polyethylene. Further still, the blank can comprise an aperture in the central portion. Even further still, Velcro® can be attached to the interior surface for adding padding and Velcro® is attached to the exterior surface for mating with a Velcro® strap. The blank can have a central portion configured to at least partially brace and extend at least partially around the neck of the user.

In one aspect, the blank can comprise a front blank, with the upper portion of the front blank corresponding to a chin of a user, and with the lower portion of the front blank corresponding to an upper chest of the user. Alternatively, the blank can comprise a back blank, with the upper portion of the back blank corresponding to an occipital lobe of the user, and the lower portion of the back blank corresponding to an upper back of the user.

In another aspect, the invention involves a blank transformable from an initial configuration to a final configuration, with the blank comprising an outer surface and an inner surface, an upper portion, a lower portion, and a central portion. The central portion having a first end and a second end that extends between the upper portion and the lower portion. The blank having a perimeter that extends from and along the first end, to the lower portion, to the second end, and to the upper portion. The blank having a double concave configuration with a first concave configuration and a second concave configuration. The first concave configuration being on the outer surface and being concave at the central portion between the upper portion and the lower portion. The second concave configuration being concave on the inner surface at the central portion between the first end and the second end.

In one aspect, the blank can either be formed of a moldable material or of a flat piece of material. The blank can be formed by vacuum forming on a blank model, drape molding, printing in a three-dimensional printer, or injection molding.

In one aspect, the casting on a blank model can include the steps of obtaining a blank mold having a neck section with a humanoid shape, applying a moldable material over the blank mold, heating the material to at least a predetermined temperature, molding the material to the mold and allowing the material to transform to the final configuration different from the initial configuration, the final configuration conforms generally to the shape of the neck section of the blank mold, and cutting the material to form the blank, with the blank having a central portion, an upper portion, and a lower portion. The upper portion and the lower portion extend outwardly from the central portion. The blank can have an interior surface wherein the central portion of the interior surface defines a substantially parabolic shaped interior. The blank can have an exterior surface with a median portion having a generally concave shape.

In one aspect, the blank can be a back blank, or the blank can be a front blank and can include a hole configured to be disposed at a ventilator connection location or laryngeal prominence of a patient's neck. Further, a combination of a front blank and a back blank are usable together to form a cervical collar and wherein the front blank and the back blank can be molded by heating the front blank and/or the back blank.

Further, in one aspect, a mold for forming a blank can comprise a neck section in a humanoid shape, a center portion having a first width, an upper portion having a second width, the second width being larger than the first width, and a lower portion having a third width, with the third width being larger than the second width.

In one aspect, the blank can be a front blank and the mold can comprise a front mold for forming the front blank. The neck section can include a chin portion, a neck portion, and an upper chest portion, with the chin portion corresponding to the upper portion, the neck portion corresponding to the center portion, and the upper chest portion corresponding to the lower portion of the front mold.

In one aspect, the blank can be a back blank and the mold can comprise a back mold for forming the back blank. The neck section can include a lower head portion, a neck portion, and an upper back portion, with the lower head portion corresponding to the upper portion, the neck portion corresponding to the center portion, and the upper back portion corresponding to the lower portion of the back mold.

In one aspect, the mold can be made from plaster, wood, metal, or composite material. The front mold can include an outline of the front blank, with the outline comprising an upper edge in the upper portion, a lower edge in the lower portion, and a substantially oval outline in the center portion. The back mold can include an outline of the back blank, with the outline comprising an upper edge in the upper portion and a lower edge in the lower portion.

In one aspect, a method for making a blank can comprise the steps of obtaining a blank mold having a neck section with a humanoid shape, applying a malleable material over the blank mold, heating the material to at least a predetermined temperature, the material having an initial configuration, molding the material to the mold and allowing the material to transform to a final configuration different from the initial configuration, the final configuration conforms generally to the shape of the neck section of the blank mold, and cutting the material to form the blank. The blank can have a central portion, an upper portion, and a lower portion. The upper portion and the lower portion can extend outwardly from the central portion. The blank can have an interior surface wherein the central portion of the interior surface defines a substantially parabolic shaped interior. The blank can have an exterior surface with a median portion having a generally concave shape.

In one aspect, the method can further comprise the step of removing the blank from the mold. The method can further comprise creating an outline of the blank on the mold. The method can further comprise buffing or polishing the blank after cutting the material to form the blank. Optionally, the predetermined temperature can be about 330° F.

In one aspect, the blank formed from the mold can be a front blank and the mold can be a front mold for forming the front blank. The neck portion can include a chin portion, a neck portion, and an upper chest portion, with the chin portion corresponding to the upper portion, the neck portion corresponding to the center portion, and the upper chest portion corresponding to the lower portion of the front mold. The front mold can include an outline of the front blank. The outline can comprise an upper edge in the upper portion, a lower edge in the lower portion, and a substantially oval outline in the center portion.

In one aspect, the blank formed from the mold can be a back blank and the mold can comprise a back mold for forming the back blank. The neck portion can include a lower head portion, a neck portion, and an upper back portion, with the lower head portion corresponding to the upper portion, the neck portion corresponding to the center portion, and the upper back portion corresponding to the lower portion of the back mold. The back mold can include an outline of the back blank. The outline can comprise an upper edge in the upper portion and a lower edge in the lower portion.

In another aspect, the present invention includes a method for forming a blank mold sized and configured to form standardized front and back blanks, the blanks made from the blank mold, and the method of forming the front and/or back blank from the blank mold. The front and back blanks are capable of being utilized to form custom fabricated collars, such as a custom fabricated collar made from a cervical collar brace kit similar to the one described herein.

The method of forming the front and back blanks can be performed on an already formed blank mold, or can involve creating a new blank mold. Once the blank mold is selected or formed, a material (such as a low density polyethylene) is applied onto or otherwise disposed over the blank mold. The material can be heated or otherwise conformed substantially to at least a portion of the blank mold. The front or back blank can then be cut or otherwise separated from the conformed material, typically by following an outline or contour(s). If the blank being formed is a front blank, before, after, or simultaneous with the cutting of the material, a hole can be cut from a central portion thereof to provide an opening for an Adam's apple, breathing tube, or other use. The front blank and/or back blank can be included in a collar brace kit or can be otherwise provided to form a custom collar brace for an individual patient. The blank can be heat molded, drape molded, vacuum molded, injection molded, poured, three-dimensional image printing, or any other technique.

BRIEF DESCRIPTION OF THE DRAWINGS

The accompanying drawings, which are included to provide a further understanding of the invention, are incorporated in and constitute a part of this specification, illustrate embodiments of the invention, and together with the detailed description, serve to explain the principles of the invention. No attempt is made to show structural details of the invention in more detail than may be necessary for a fundamental understanding of the invention and the various ways in which it may be practiced. In addition, it will be understood by those skilled in the art that the embodiments of the invention and the various features thereof discussed below are explained in detail with reference to non-limiting embodiments and examples that are described and/or illustrated in the accompanying drawings. It should be noted that the features illustrated in the drawings are not necessarily drawn to scale, and features of one embodiment may be employed with other embodiments as the skilled artisan would recognize, even if not explicitly stated herein. Descriptions of certain components and processing techniques further may be omitted so as to not unnecessarily obscure the embodiments of the invention.

Additional features, advantages, and embodiments of the disclosure may be set forth or apparent from consideration of the following detailed description, drawings, and claims. Moreover, it is to be understood that both the foregoing the following detailed description are exemplary and intended to provide further explanation without limiting the scope of the disclosure as claimed.

FIGS. 5A-5G show various views of a front molding blank.

DETAILED DESCRIPTION OF INVENTION

Figure 1:
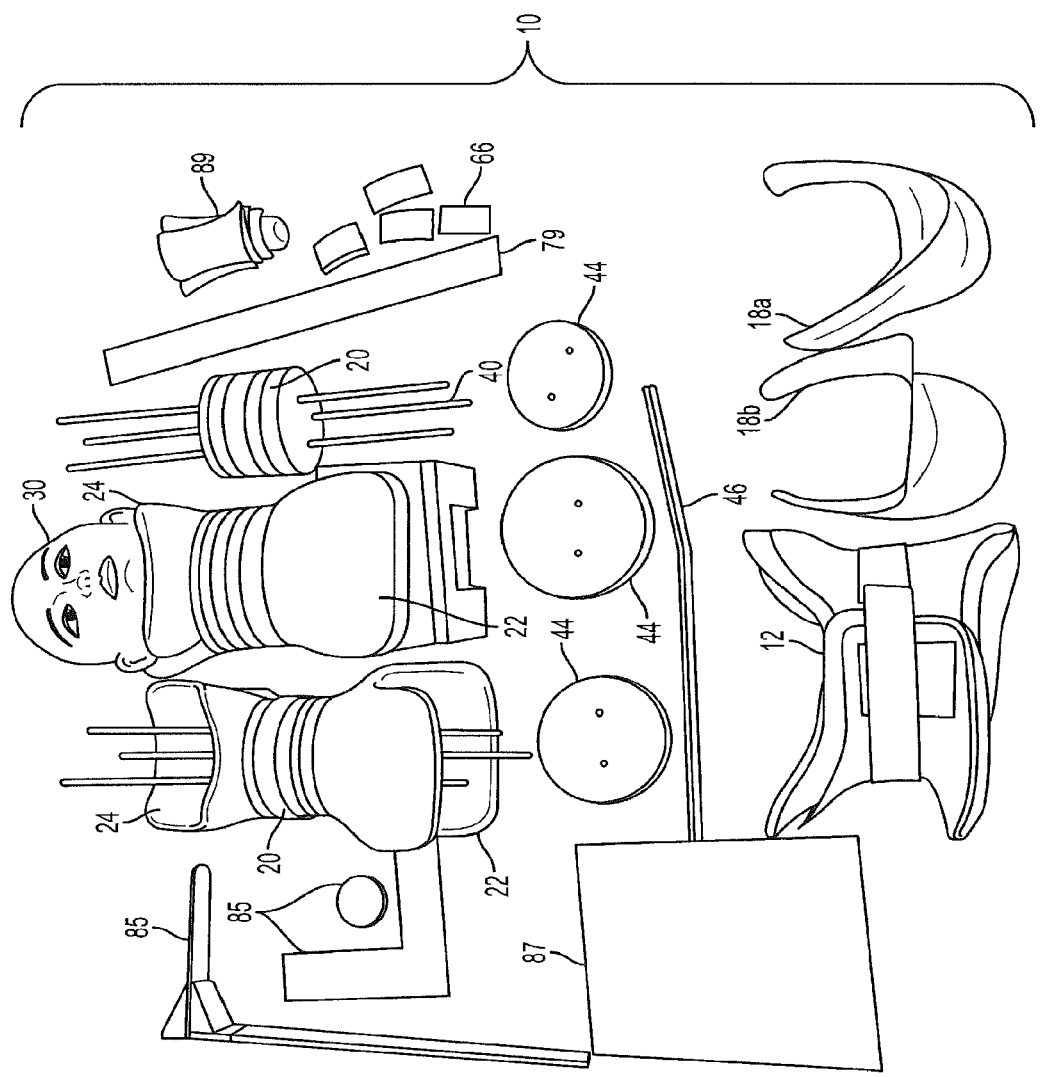
FIG. 1 is a perspective view of a brace kit.

Referring now to the drawings in which like numerals indicate like parts throughout the several views, FIG. 1 shows a prefabricated brace kit, generally indicated at 10, for creating a collar or neck brace 12 specifically sized and molded to model an individual. The brace kit 10 includes a number of items useable to form a model to mimic a patient needing a collar brace. The model is adjustable in neck height, width, and flexion/extension angles. While FIG. 1 shows several items capable of being in the kit 10, one of ordinary skill in the art will recognize that the kit 10 can include more or less items without departing from or limiting the scope of the present invention. The items shown in kit 10 in FIG. 1 are exemplary only and should not be limiting in any manner.

As illustrated in FIG. 1, the brace kit 10 includes a model or mold 16 (shown in FIG. 2), pre-shaped front and back molding blanks 18a, 18b, dowel rod(s) 40, wedge shaped neck blocks 44, flexion rod(s) 46, a head portion 30, and a pad kit. The brace kit 10 may also include various sized neck blocks 20, chest bases 22, and chin and occipital bases 24 used to build a custom model for molding the front and back blanks 18a, 18b specifically for individual patients. As shown in FIG. 1, the kit 10 includes a pad kit that contains padding 68 (shown in FIG. 11) for the front and back blanks 18a 18b, Velcro® attachments 66, and a Velcro® strap 79 sized to wrap around and secure the front blank and the back blank using Velcro® attachments 66. When attached as a unit, the front blank and back blank form a custom molded collar brace 12 (shown in FIG. 12). The kit may also include wrapping material such as an ace bandage wrap 89, a heating device 84 (such as a heat gun, shown in FIG. 9), and measuring devices 85 (such as measuring tape, calipers, and/or other measuring tools). Also, the kit may include a measurement form 87 to record measurements of a patient. In an alternative embodiment, an expandable bladder apparatus (not shown) can be used in place of the neck blocks, with the expandable bladder apparatus capable of being sized to mimic a patient's measurements.

Figure 2:
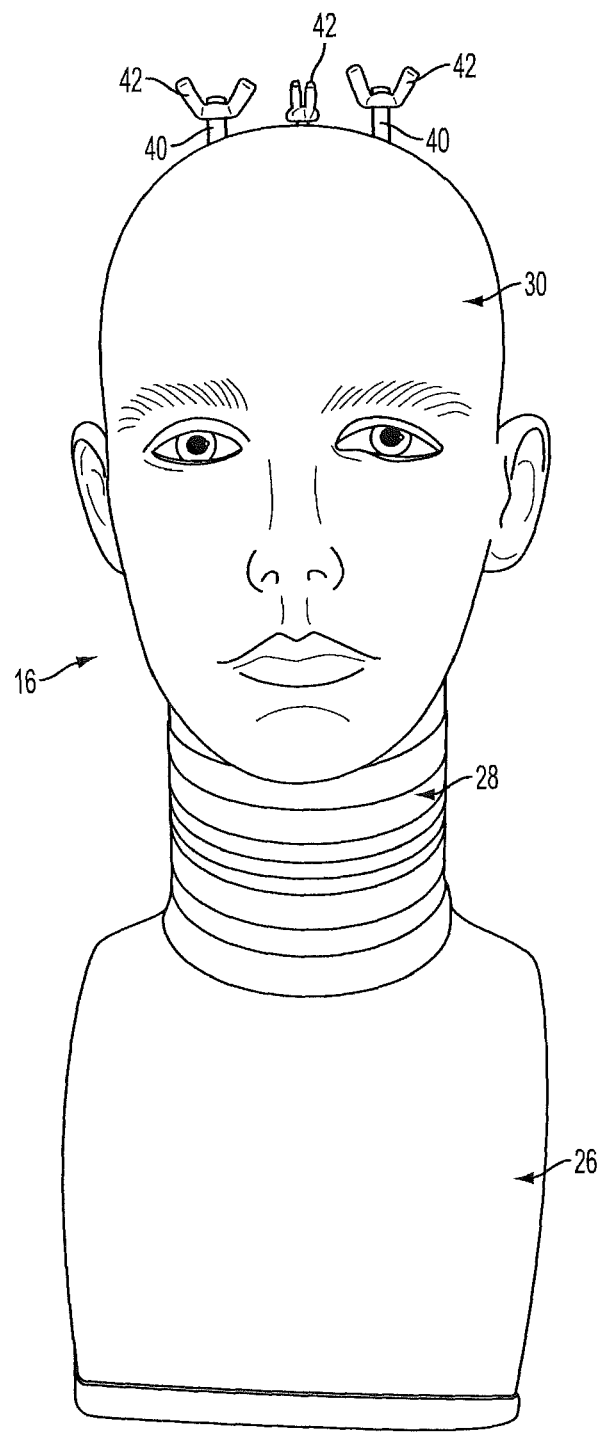
FIG. 2 is a perspective view of a model with neck blocks installed.

In this specification, the terms "front", "back", "lower," "bottom," "upper" and "top" as used herein indicate orientations determined in relation to an exemplary model 16. As illustrated in FIG. 2, the model 16 includes a chest base 26, a neck portion 28, and a head portion 30. The head and neck portions 30, 28 are removable from the chest base 26. In the exemplary illustrated embodiment, the model 16 has three channels 32 (shown in FIG. 7) that extend through the model 16 from the crown of the head portion 30 to the bottom of the chest base 26. Up to three dowel rods 40 can be received in the channels 32 to extend there through. The dowel rods 40, as shown in FIG. 2, are substantially straight, but could be formed in other configurations as detailed herein. Securing means, such as wing nuts 42, may be used to secure the dowel rods 40 within the channels 32, thereby securing the head portion 30, neck portion 28, and chest base 26 together. While three channels 32 are shown in the figures, any number of channels can be used to form the model 16. Additionally and/or alternatively, other methods of attaching or releasably securing portions of the model 16 together are within the scope of the invention. For example, such alternate securing methods include Velcro hook and loop fasteners, such as Velcro®, tongue-in-groove sliding attachment, snaps, stays, etc. Further, the model 16 may have more or less channels, with a corresponding number or fewer dowel rods, without departing from the disclosure, for instance two channels accommodating up to two dowel rods may be used. Alternatively, one large rod positioned in the center of the model could be used without departing from the disclosure. Further still, no dowel rods can be used with the model 16 portions being secured by Velcro hook and loop fasteners, such as Velcro®, tongue-in-groove sliding attachment, snaps, stays, etc. without departing from the disclosure.

In one embodiment, various sized neck blocks 20 are capable of being installed on or removed from the neck portion 28 of the model 16. The kit 10 may include several pre-sized neck blocks 20 of various thicknesses or heights in a range of diameters. Typically most patients fall within a range of neck diameters between 13¾-in and 18½-in. The neck blocks 20 may range in thickness, for instance, between ¼-in. to 2-in., or may have larger or smaller thickness without departing from the disclosure. As shown in the brace kit 10 of FIG. 1, the blocks 20 preferably have a diameter between about 12-in and about 19-in, with exemplary diameters as shown having diameters 13¾-in, 16-in, and 18½-in. In an alternative embodiment, the neck blocks may be sized or formed to specific measurements of each patient and the kit can include blocks of greater or smaller sized diameter to fit all sizes of children and adults. Although not shown in detail in the figures, the kit 10 also includes various wedge shaped neck blocks 44 and flexed dowel rod(s) 46 to accommodate special cases where the patient has uncorrectable flexion of the neck, such as from osteoporosis. The neck blocks 20, 44 may be formed from any appropriate material, including, for example, cloud EVA foam, plastic, wood, or any type of acceptable material that can be cut, poured, or formed. The neck blocks and flexed dowel rod(s) can be utilized in the manner and methods described herein to build a model to mimic a patent with uncorrectable flexion of the neck.

Although the head portion 30 may include a full head portion, an entire head of the model is not required. However, in a preferred embodiment, the lower portion of the head of the model should generally include a chin and occipital lobe section of the head portion 30.

Figure 3:
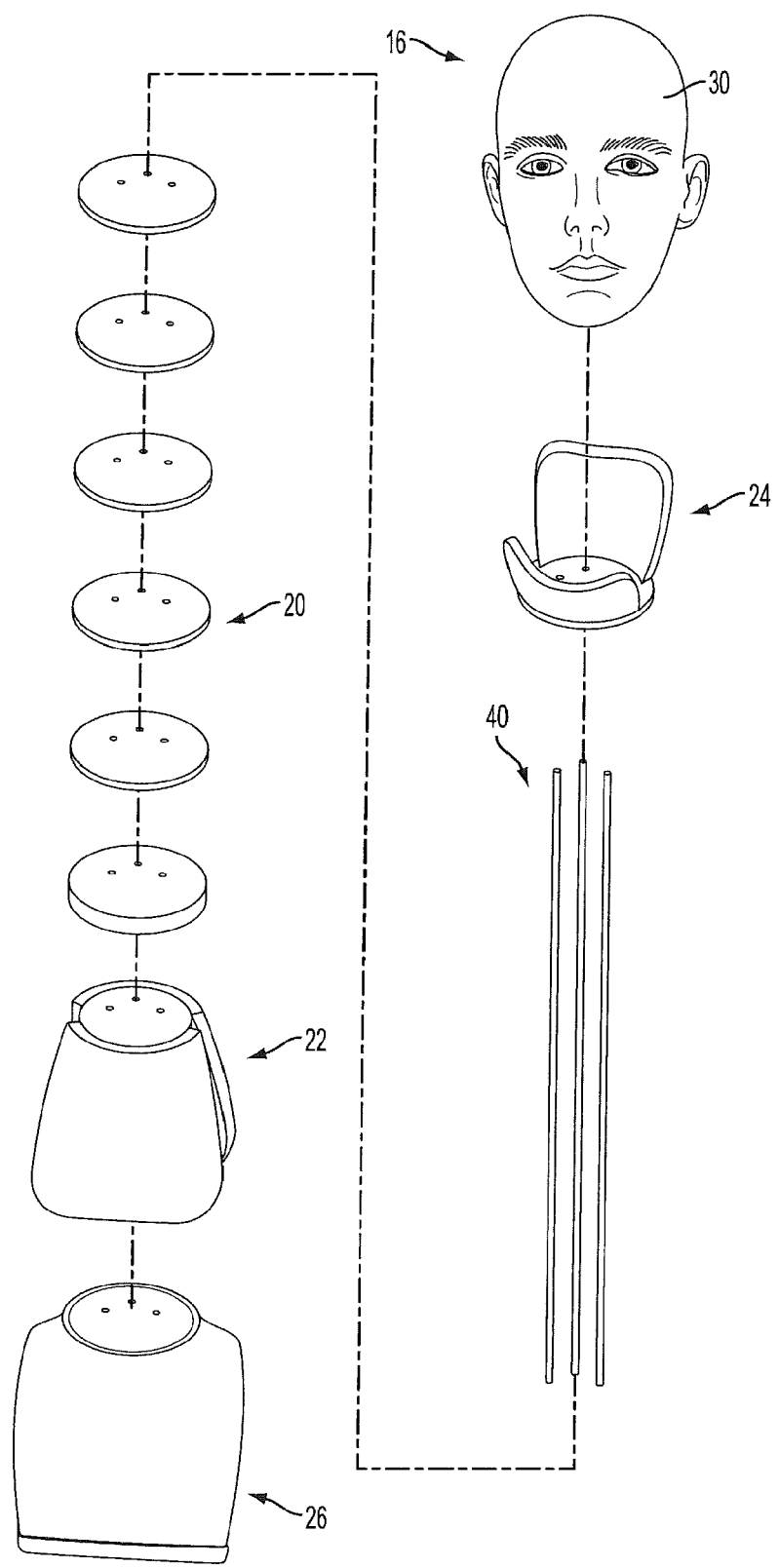
FIG. 3 is an exploded perspective view of a model with neck blocks, a chest base, and a chin and occipital base.
Figure 4A:
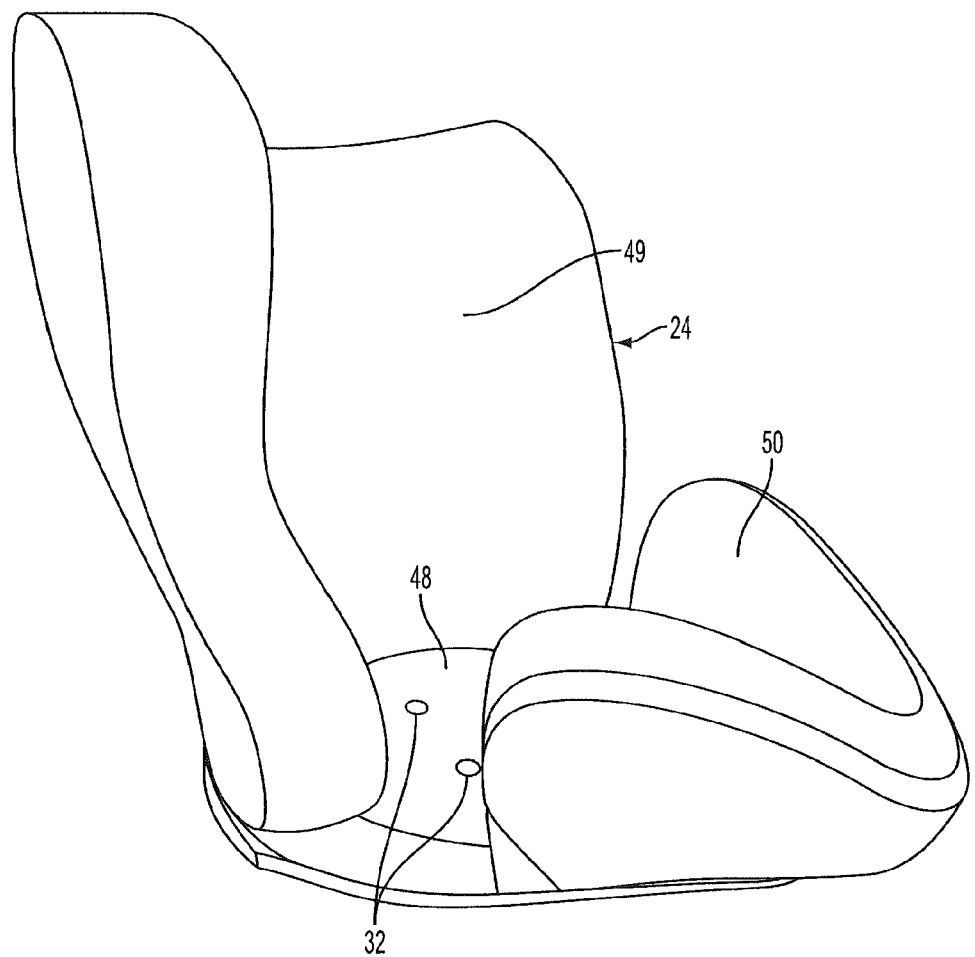
FIG. 4A is a perspective view of a chin and occipital base.
Figure 4B:
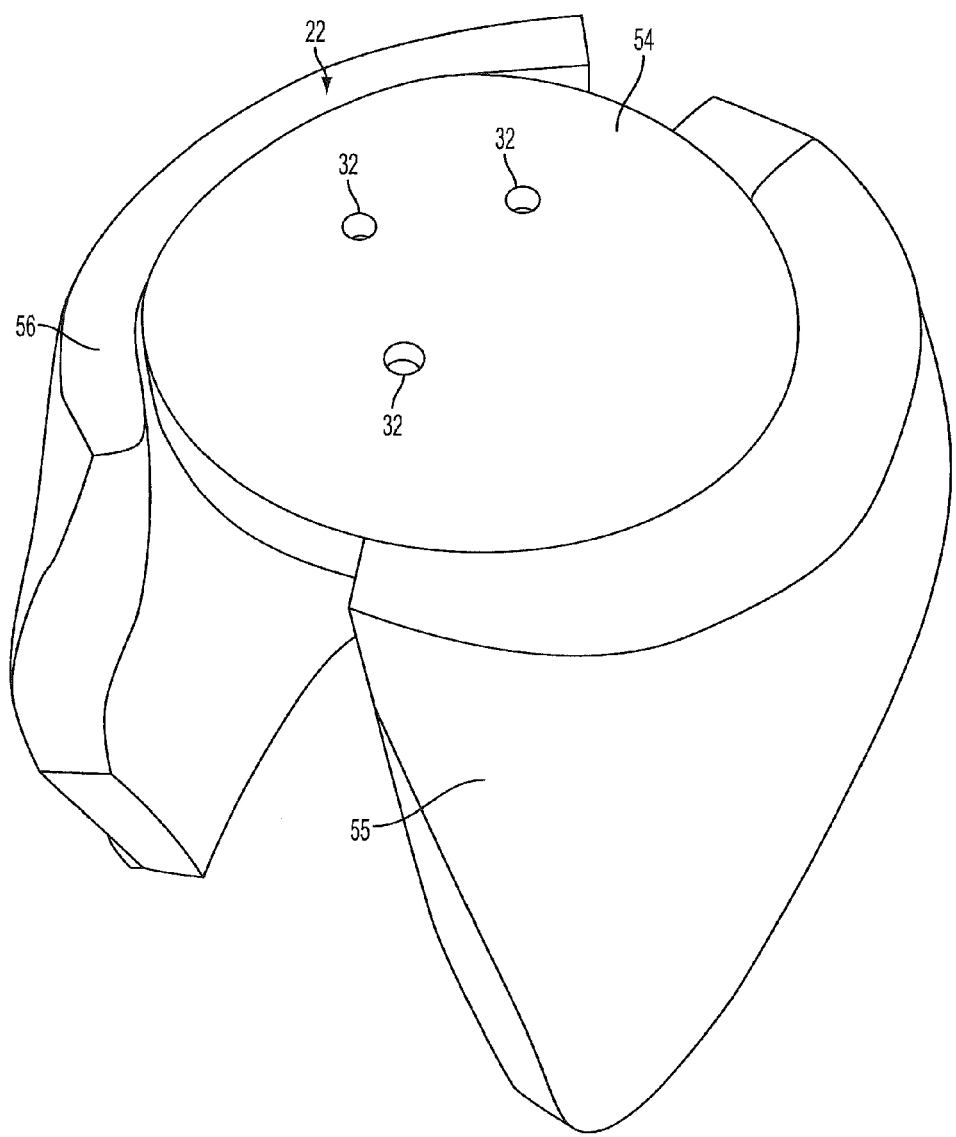
FIG. 4B is a perspective view of a chest base.
Figure 5A:
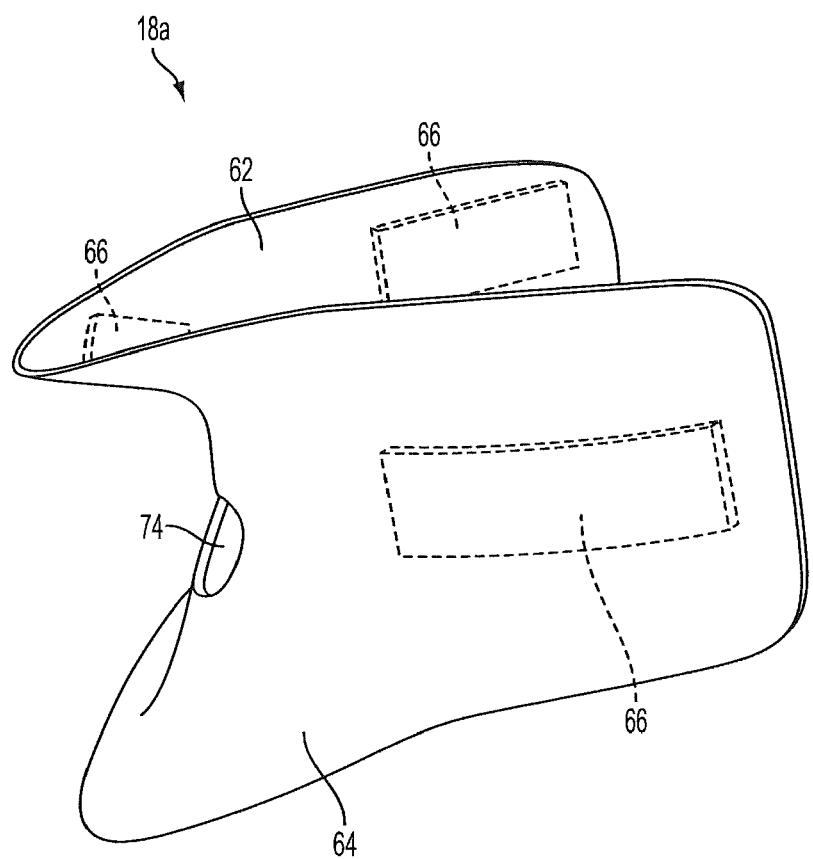
Figure 5B:
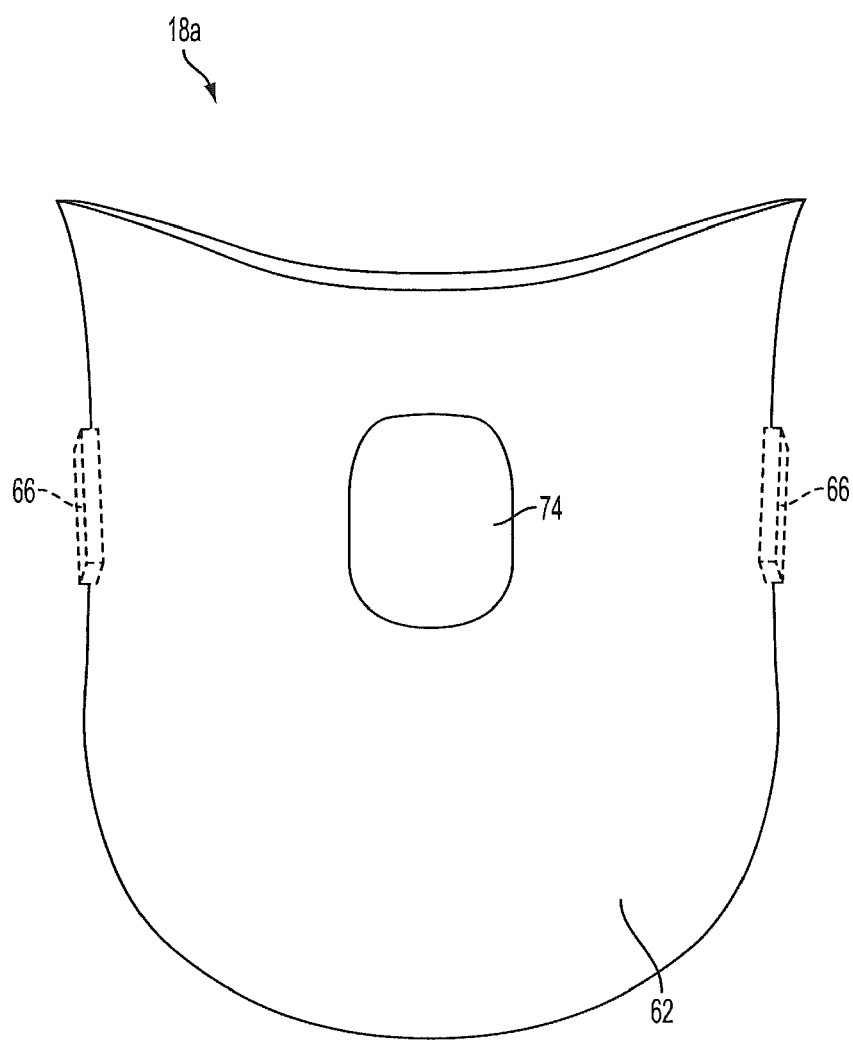
Figure 5C:
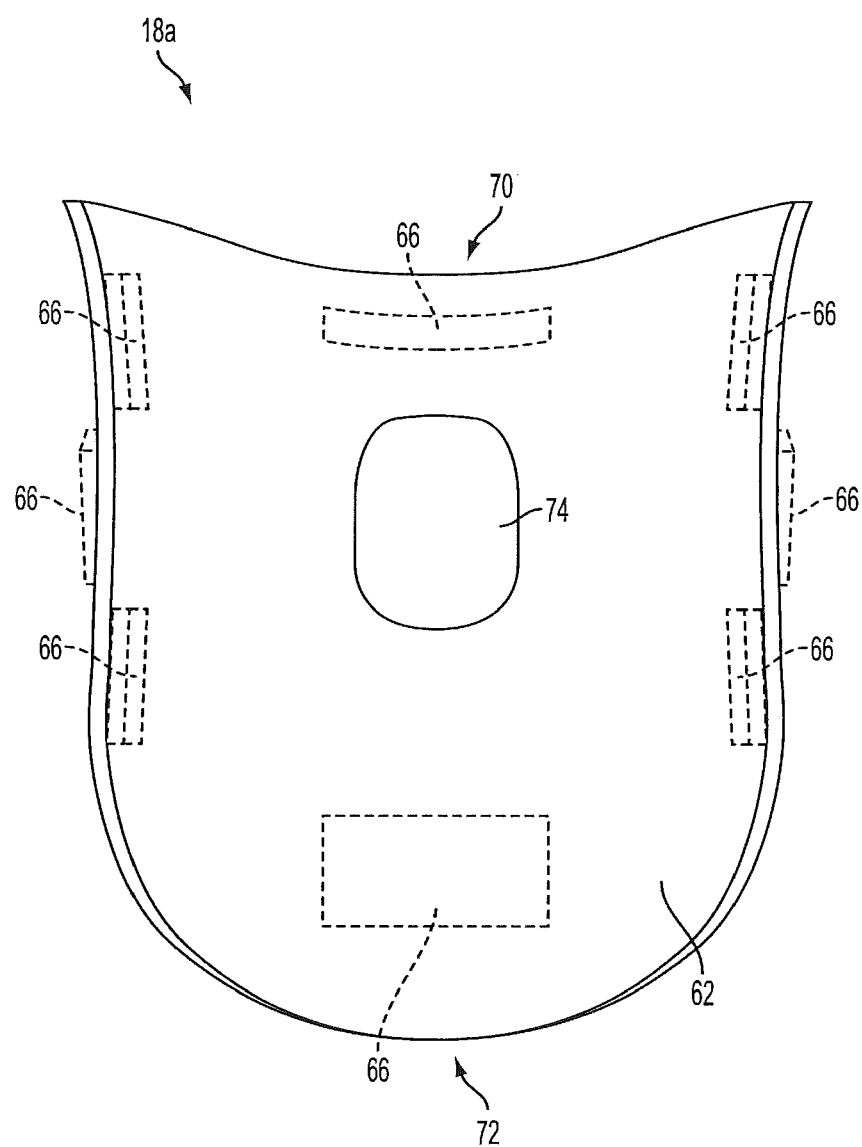
Figure 5F:
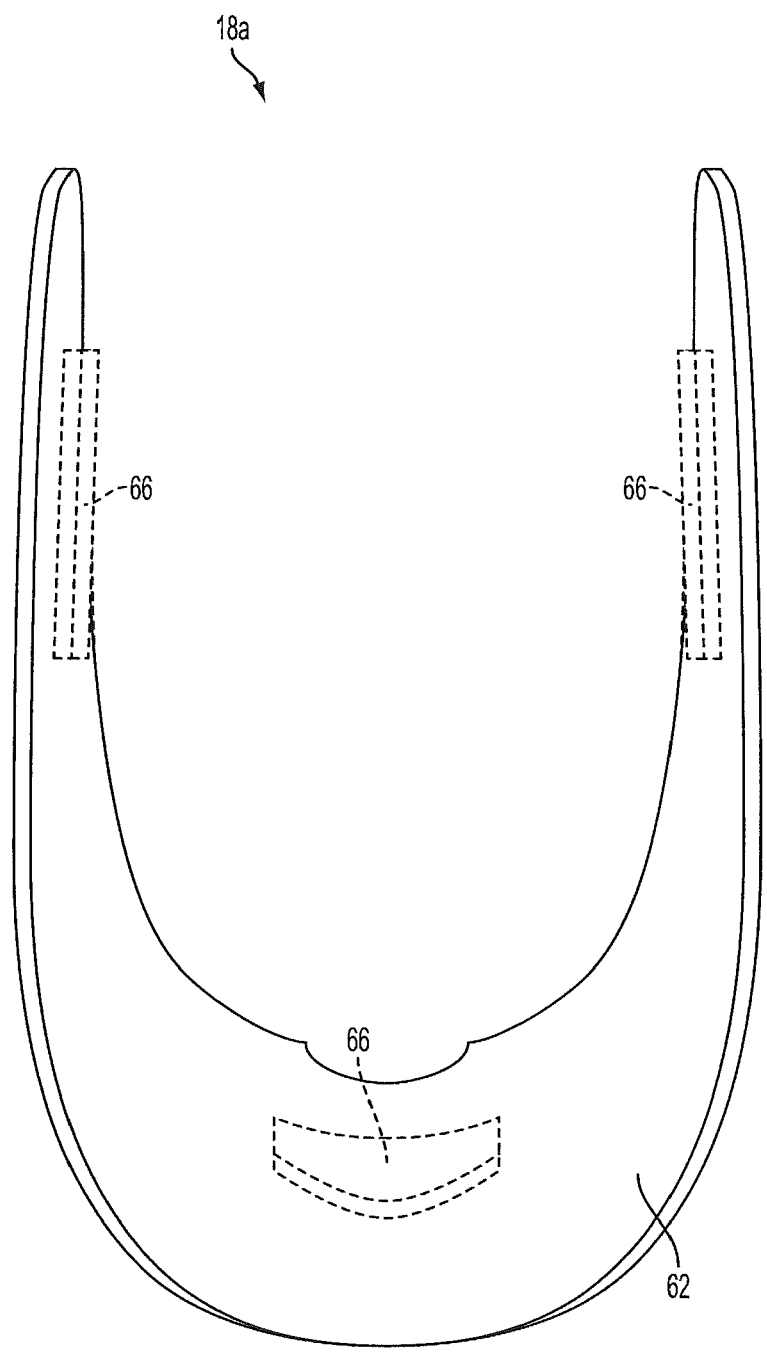
Figure 5G:
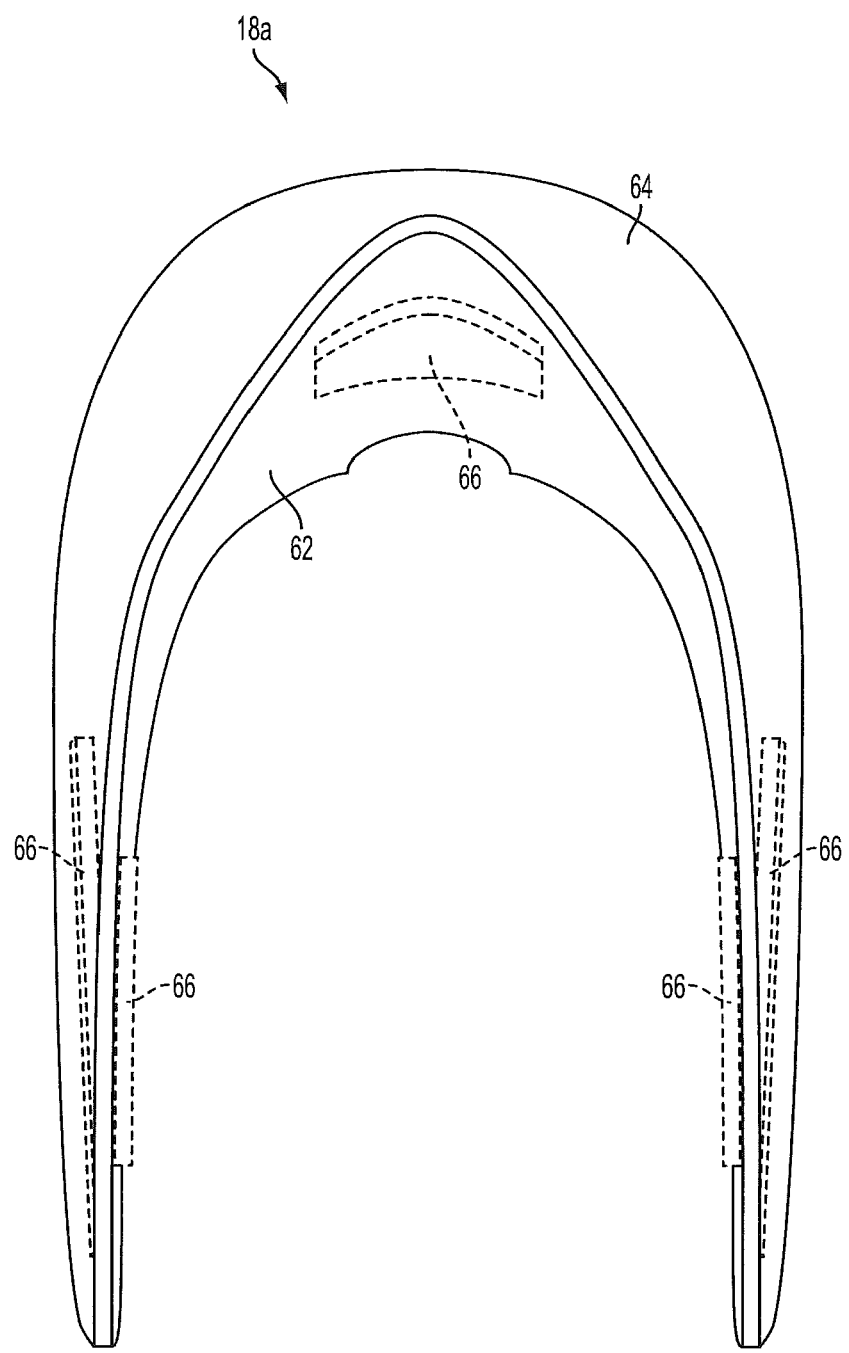
Figure 6A:
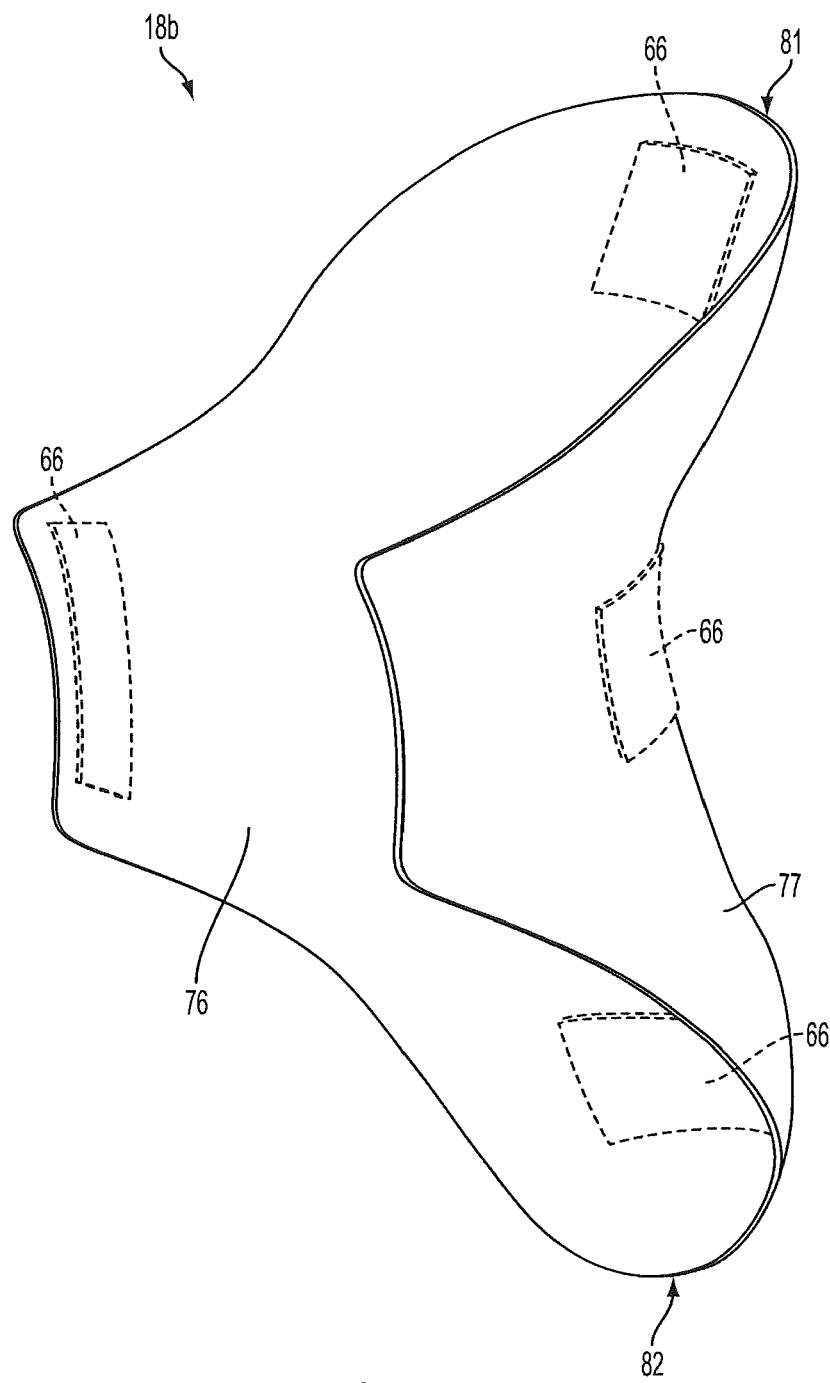
FIGS. 6A-6G show various views of a back molding blank.
Figure 6B:
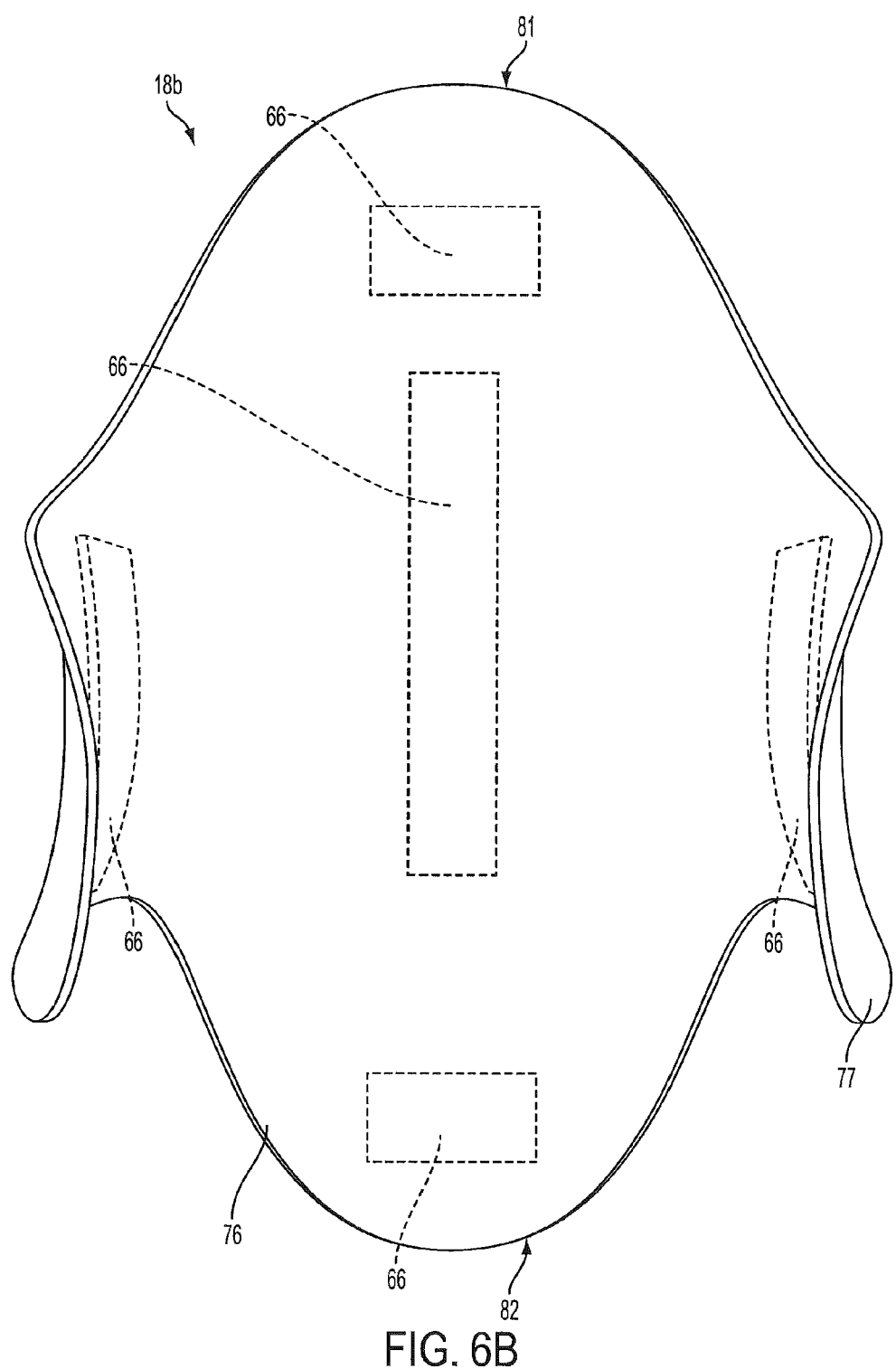
Figure 6C:
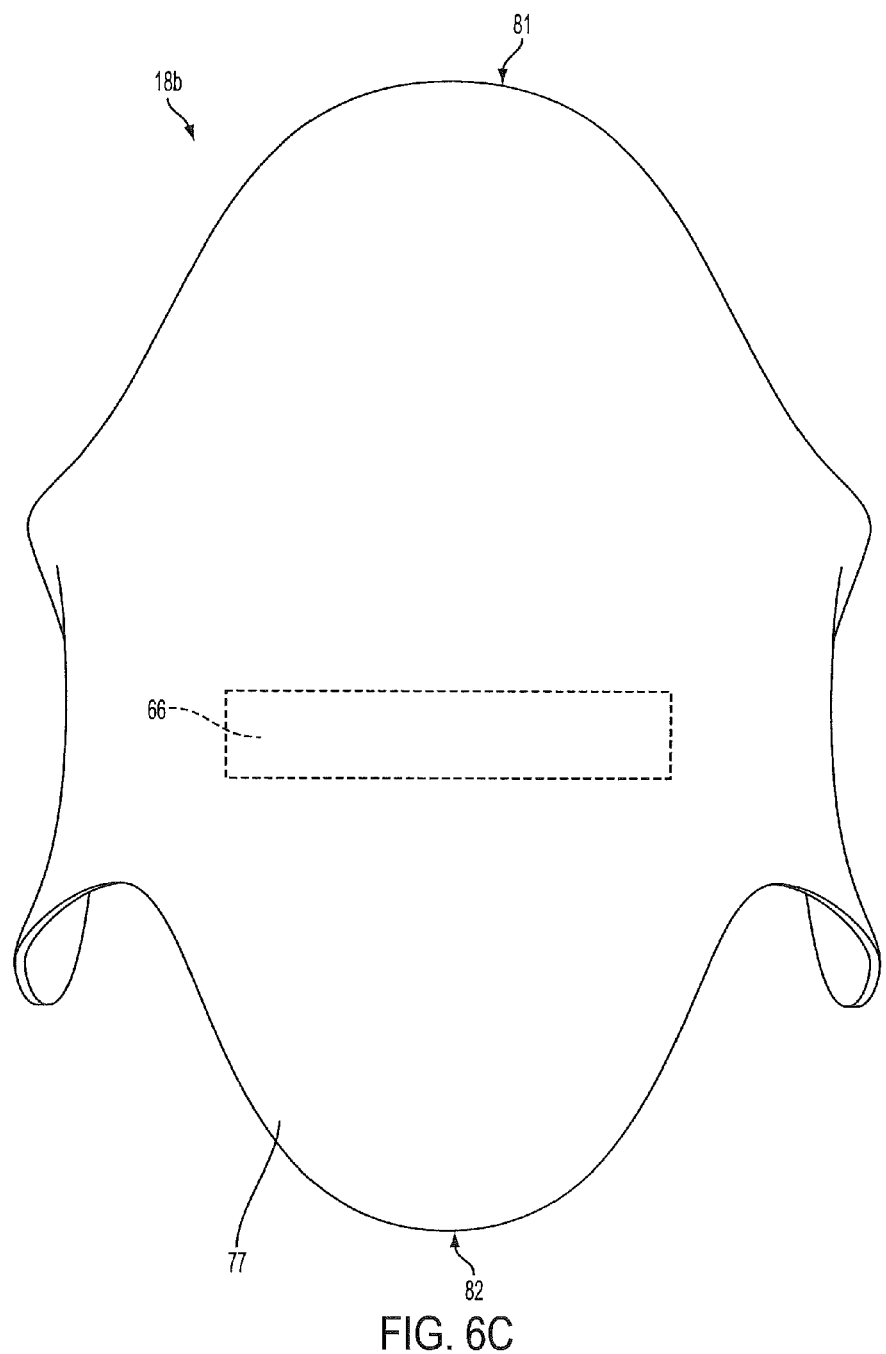
Figure 6D:
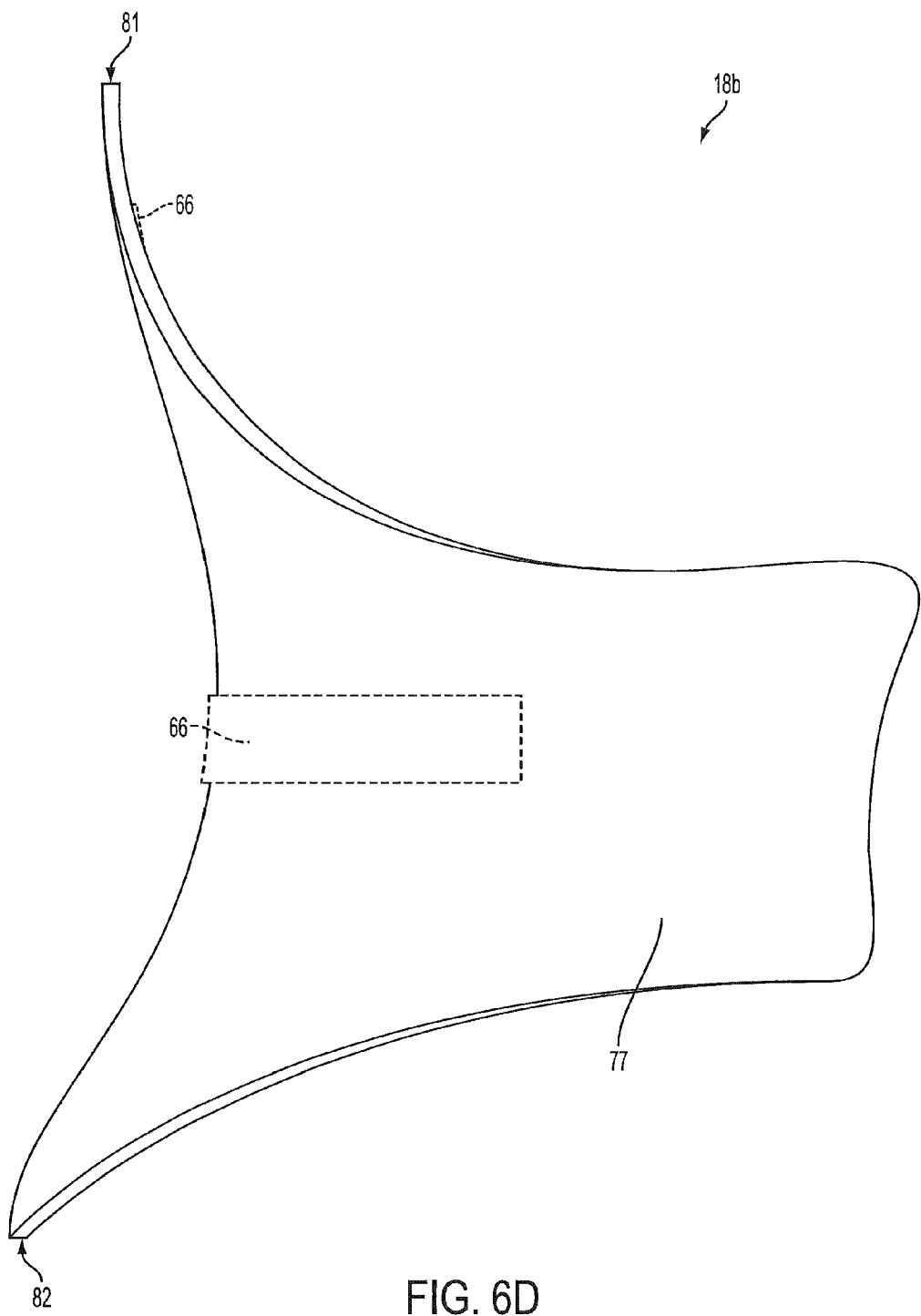
Figure 6E:
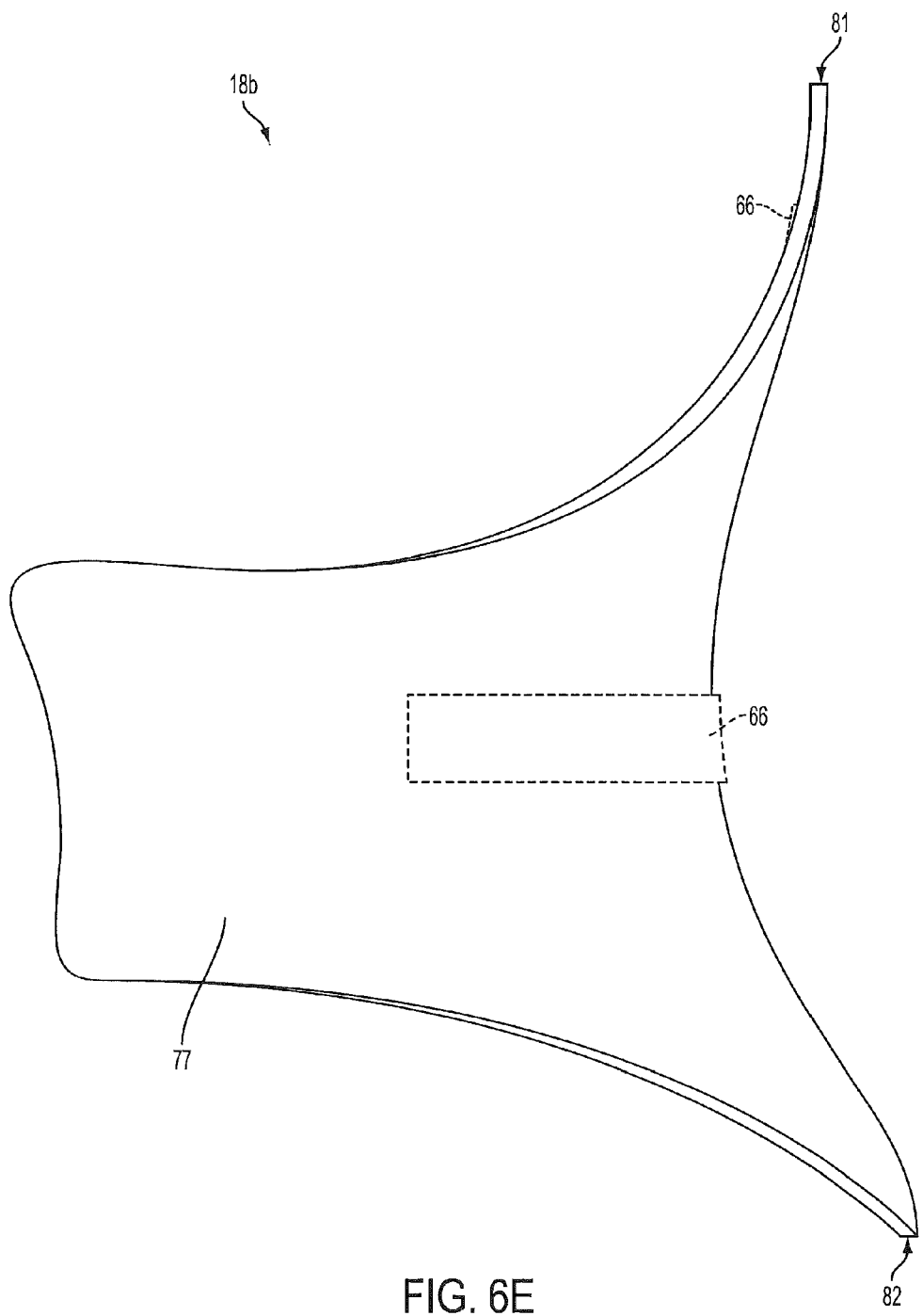
Figure 6F:
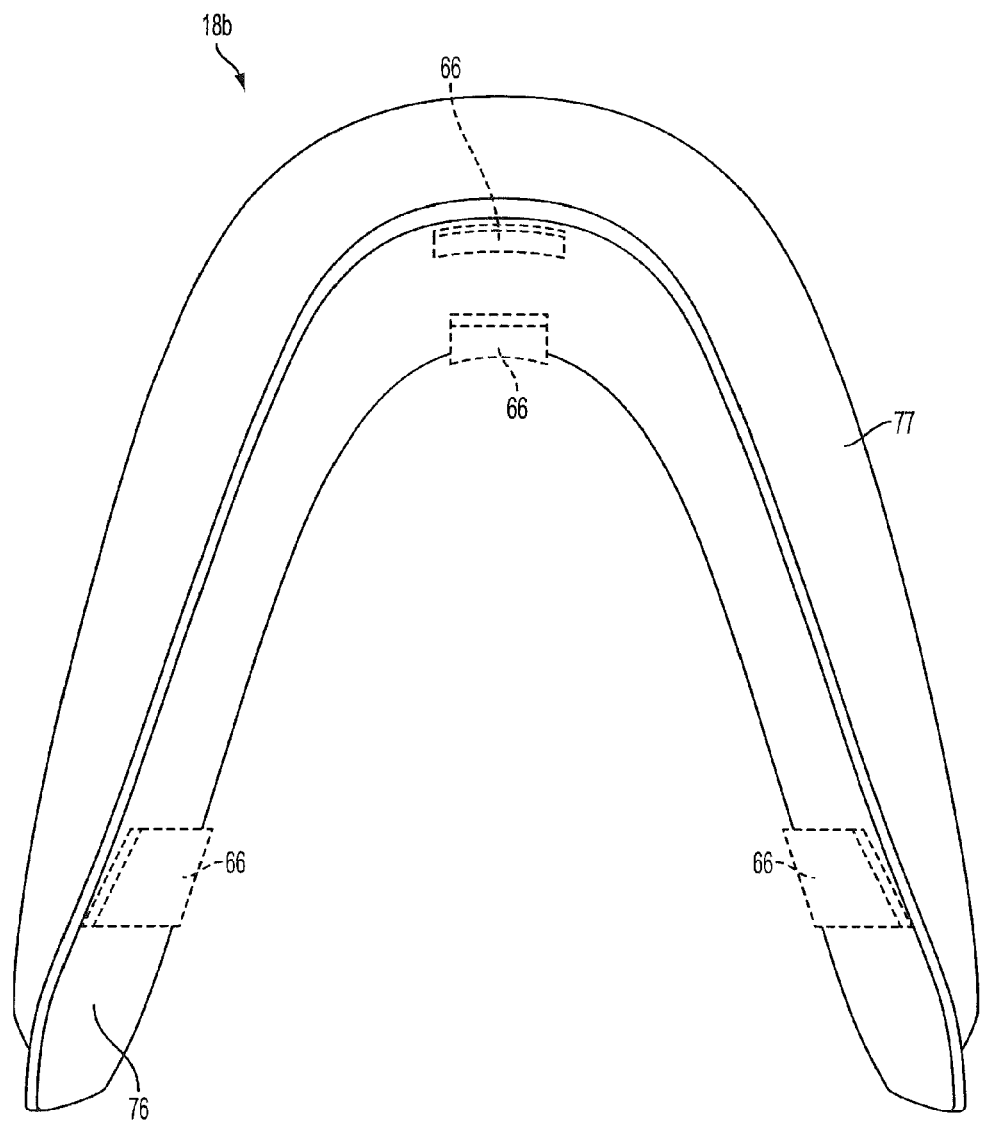
Figure 6G:
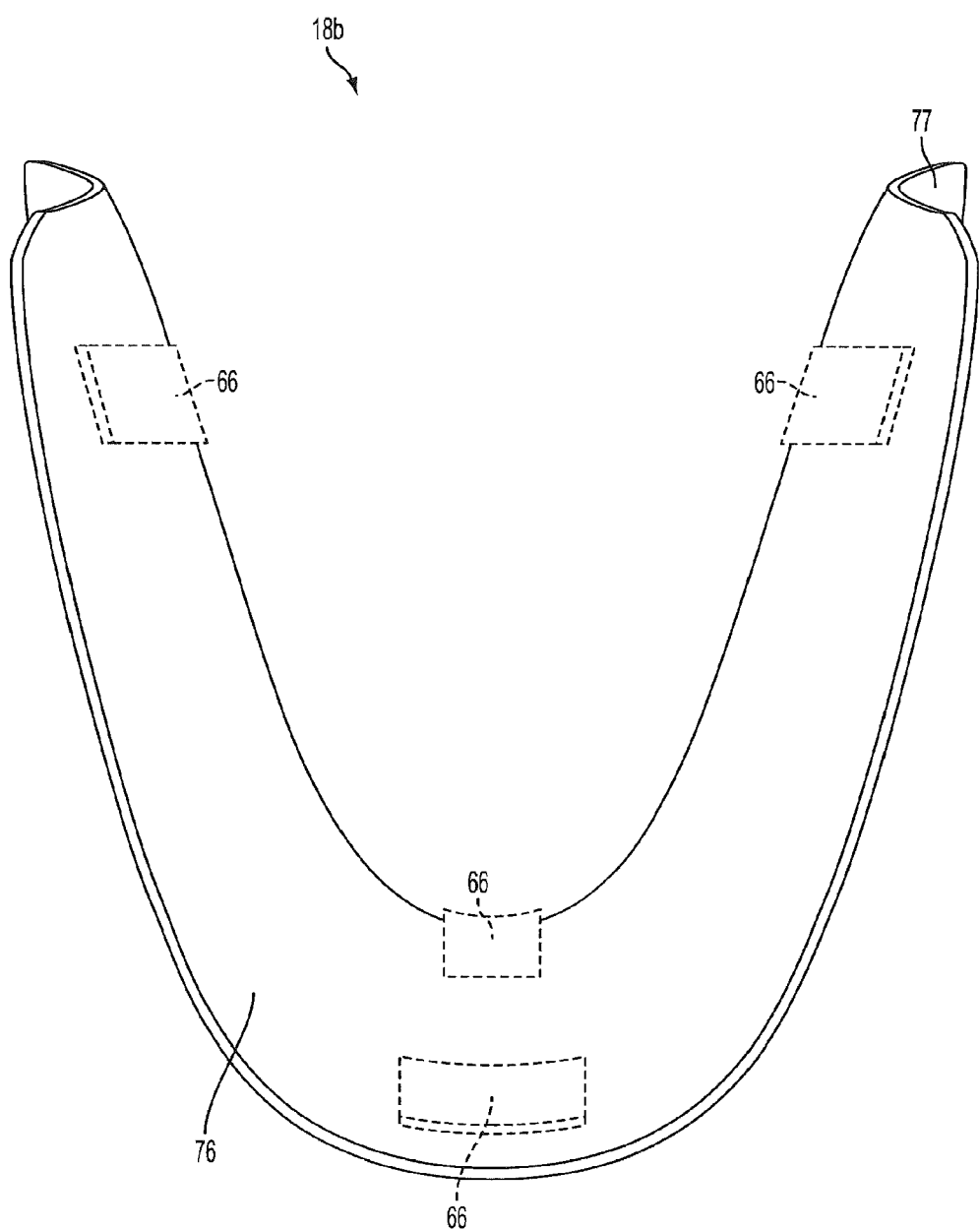

As shown in FIGS. 3, 4A, and 4B, the kit typically also includes various sized chest bases 22 and various sized chin and occipital bases 24 that correspond to and fit with the base 26 and head 30, respectively, to increase the size of the chin and occipital area and the size of the base to correspond more appropriately to generally larger sized neck blocks 20 to more closely mimic a larger sized patient.

As shown in FIG. 4A, the kit typically also includes various sized chin and occipital bases 24 that fit over the head 30 to increase the size of the chin and occipital area and to correspond more appropriately to the various (generally larger) sized neck blocks 20. For instance, if an analogous neck block 20 is 18½-in, the chin and occipital base 24 should be utilized to correspond to the 18½-in sized neck block, especially if appropriate to more closely mimic a user. The chin and occipital base 24 shown in FIG. 4A includes a base portion 48 with channels 32 allowing attachment of the chin and occipital base 24 to the model 16. The base portion 48 of the chin and occipital base 24 has an occipital portion 49 and a chin portion 50, both of which are sized to correspond to respective neck blocks 20. The chin and occipital base 24 may be formed from any appropriate material, including, for example, cloud EVA foam, plastic, wood, or any type of acceptable material that can be cut, poured, or formed.

As shown in FIG. 4B, the kit may include various sized chest bases 22 that fit over the chest base 26 to increase the size of the chest to correspond appropriately to the respective sized neck blocks 20. For instance, if the measured neck block is closest to 18½-in, then the chest base 26 selected will correspond to the 18½-in sized neck block. As shown in FIG. 4B, the chest base 22 includes a base portion 54 having three channels 32 for attaching the chest base 22 to the model 16. The base portion 54 has front portion 55 and a back portion 56 connected to the base portion 54. The chest base 22 may be made from cloud EVA foam, plastic, wood, or any type of acceptable material that can be cut, poured, or formed.

Having described the portions of the model, we now turn to the blanks useable on a constructed model 16 to form a custom collar. FIGS. 5A-5G show a front blank 18a having an interior 62 and an exterior 64. The interior 62 generally includes attachment means 66 such as Velcro® or other hook and loop fasteners for attaching one or more pads 68 (shown in FIG. 11) to the molded blank 18a generally after the blank 18a has been heated and formed. The front blank 18a as shown is pre-formed with a slight concave shape, and includes a top area 70 that profiles a chin and a lower area 72 that profiles a chest. The exterior 64 can also include attachment means 66 such as Velcro® for attaching the front blank 18a to the back blank 18b (shown in FIG. 12). Optionally, the front blank 18a can include a hole or aperture 74 (shown in FIG. 13), such as for receiving a ventilator connection or for providing an area through which a laryngeal prominence (Adam's apple) can extend.

FIGS. 6A-6G show a back blank 18b, which includes an interior 76 and exterior 77. The interior 76 generally includes attachment means 66 such as Velcro® or other hook and loop fasteners for attaching one or more pads to the mold before or after it has been heated and formed. The exterior 77 can also include attachment means 66 such as Velcro® for attaching the back blank 18b to the front blank 18a (shown in FIG. 12). The back blank 18b has a top area 81 generally formed to correspond to the occipital curvature of the head and a lower portion 82 generally formed to correspond to the lower portion of the neck and upper portion of the back. The interior 62 and 76 of the front and back blanks have a substantially U-shape profile or parabolic shape that generally is shaped to engage at least the neck portion of the model 16. However, the blanks 18a, 18b may be flat without departing from the disclosure.

The front blank 18a and the back blank 18b may be made out any moldable material, e.g. low density polyethylene, but other materials may be used without departing from the disclosure. Additionally, the blanks 18a and 18b can be formed in any thickness, e.g. of 3/32-inch thick as shown in the figures, but other thicknesses may be used without departing from the disclosure. An option for heat molding a flat sheet of plastic over the kit model that mimics the patient to produce the custom molded cervical collar as opposed to using blanks 18a, 18b, and/or blanks provided in the kit, are contemplated and covered by this invention, especially when used in connection with a model 16 formed according to the present invention. While the model 16 is reusable and can be configured and sized to mimic other patients, generally the blanks are not reusable with additional blank(s) 18a, 18b available from the inventor in lieu of purchasing an entire new kit, especially those formed as detailed herein.

Figure 12:
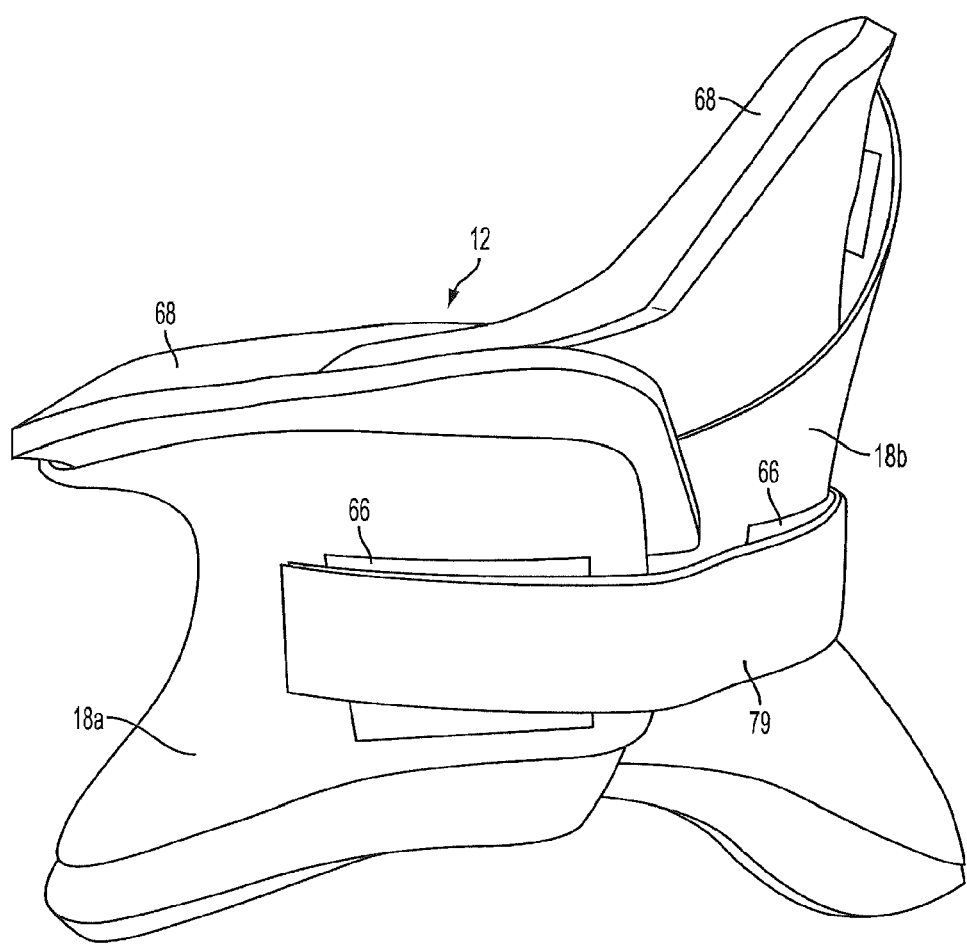
FIG. 12 is a side view of the neck brace fully assembled.
Figure 13:
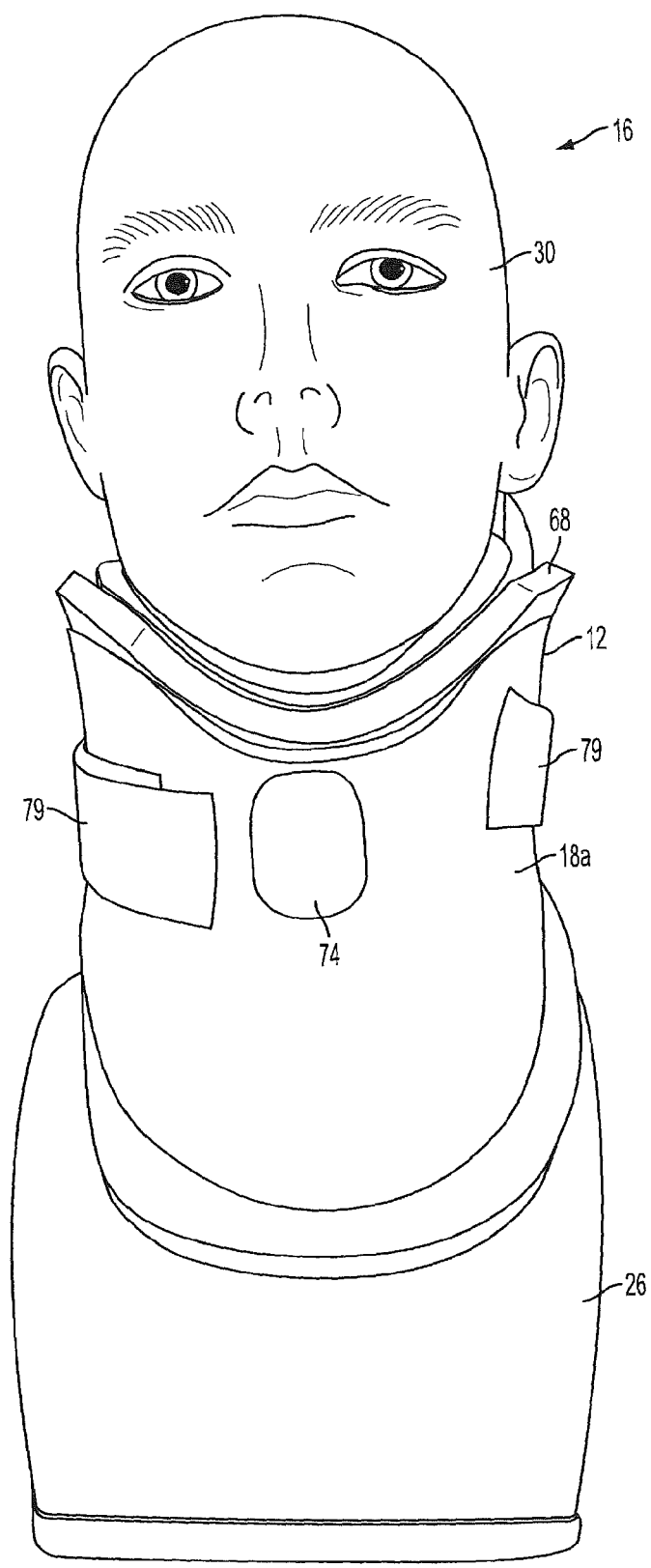
FIG. 13 is a perspective view of the neck brace mounted to the model.
Figure 14:
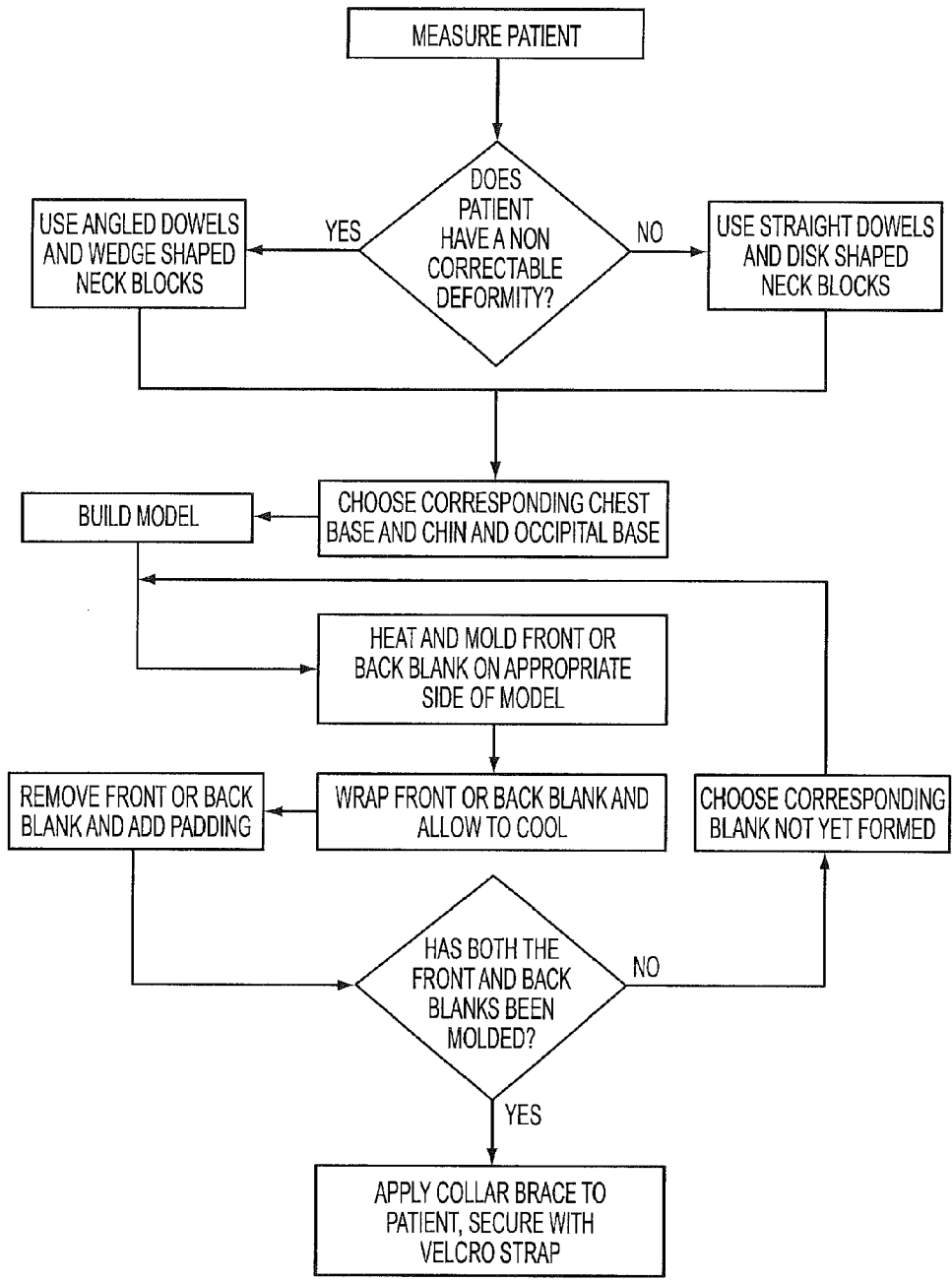
FIG. 14 is a flow chart of one exemplary method for forming a collar brace.

One exemplary method of molding the front and back blanks 18a and 18b to form the collar brace 12 is generally shown in FIGS. 7-13 and detailed in the flowchart of FIG. 14. The first step of the method is to take measurements of the patient. For exemplary purposes only, the measurements can include measuring the neck circumference and then adding one-inch to account for padding width, measuring the distance from the bottom of the chin to the sternal notch using an appropriate measurement device (an exemplary measurement device is shown at 85 in FIG. 1), measuring the distance of the occiput to the spinous process of C7 vertebra, measuring the distance from the bottom of the earlobe to the highest part of the shoulder, measuring the distance of the neck anterior to the neck posterior, and measuring the distance of the neck medial to the neck lateral. The padding is optional, generally for comfort and support, and the brace could be formed without the padding. Further, the padding can be thicker or thinner than the one-inch provided for in the exemplary padding shown in the figures and described herein. If a thicker or thinner padding is to be used, the offset/addition to the neck circumference measurement will be greater or less, respectively.

Any additional observation, e.g. if the neck has a non correctable flexion deformity can also be noted. If the patient has a non correctable flexion deformity, wedge shaped neck blocks 44 and flexed dowel rods 46 can be used to form the neck portion of the model 16 to more directly mimic the neck portion of an individual with such non-correctable flexion deformity. Further, it should be noted that, if required, dowel rods (40 or 46) can be bent further than shown or provided initially in the kit 10. Also, blocks (20 or 44) can be sized (such as by cutting or otherwise shaping) in order to approximate or model most closely an individual patient's unique physique or form.

Figure 7:
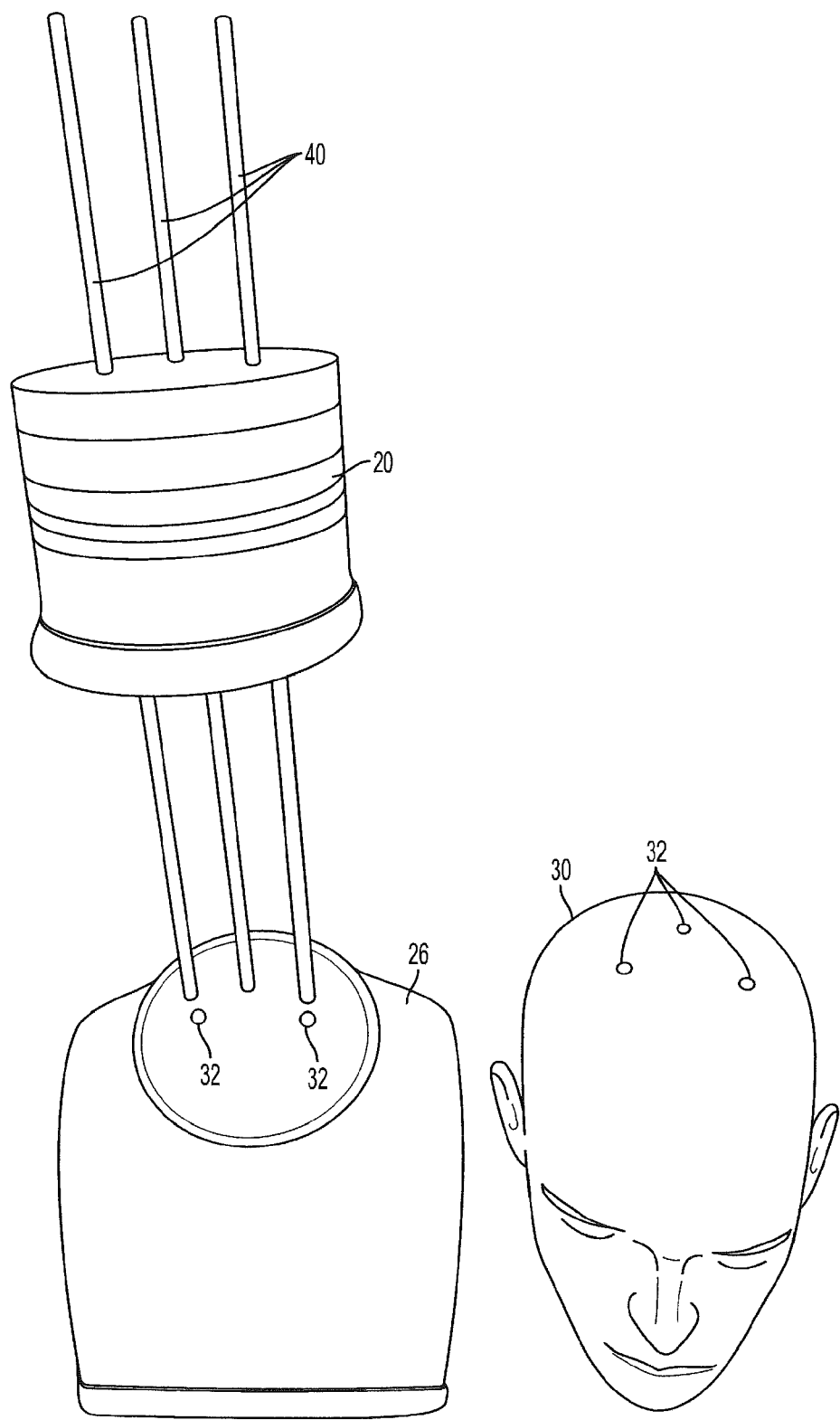
FIG. 7 is a perspective view of the neck blocks positioned on straight dowel rods to be mounted onto the model.
Figure 8:
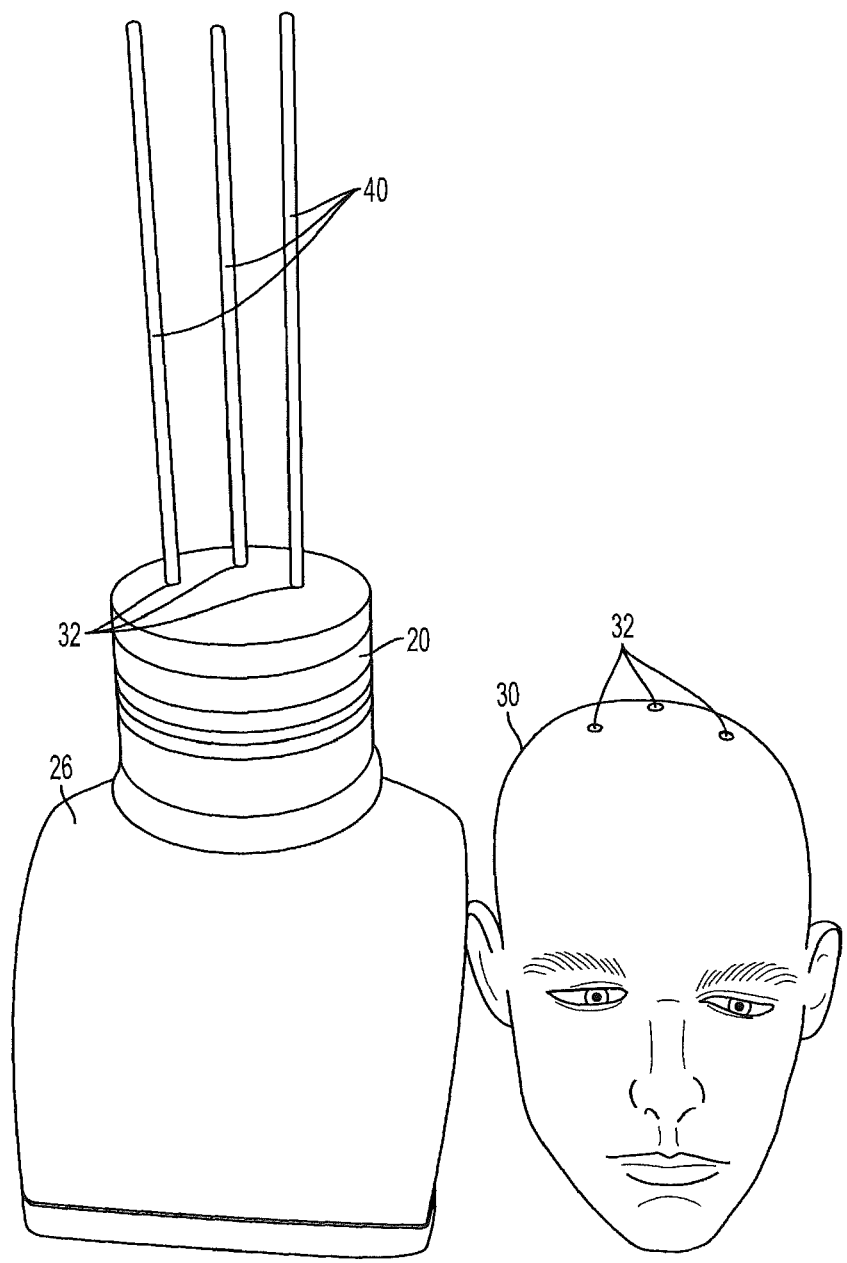
FIG. 8 is a perspective view of neck blocks mounted onto the chest base.

As illustrated in FIGS. 7-8, while the neck portion, head portion, and base portion can be attached to one another or dowel rod(s) 40 in any order, for exemplary purposes, neck blocks 20 are added to dowel rods 40 to form the neck portion 28 of the model 16 (16 and 28 are shown in FIG. 2). Then, the dowel rods 40 are aligned with the openings 32 in the chest base 26 and secured thereto. The openings/channels 32 in the head portion are aligned with the dowel rods 40 and then attached to the chest 26 and neck portion 28 to form the model 16. Wing nuts or other securing means may be added to the top and/or bottom of the dowel rods to hold the model securely together. In an alternative embodiment, if the model requires the use of a chest base 22 and occipital and chin base 24 to better mimic the patient, the dowel rod(s) 40 may be secured first to the chest base 26 and then a chest base 22 corresponding to the size of the patient may be added before the neck bases 20 are added (see FIG. 3, for example). The chin and occipital bases 24 are then added, followed by the head portion 30.

Figure 9:
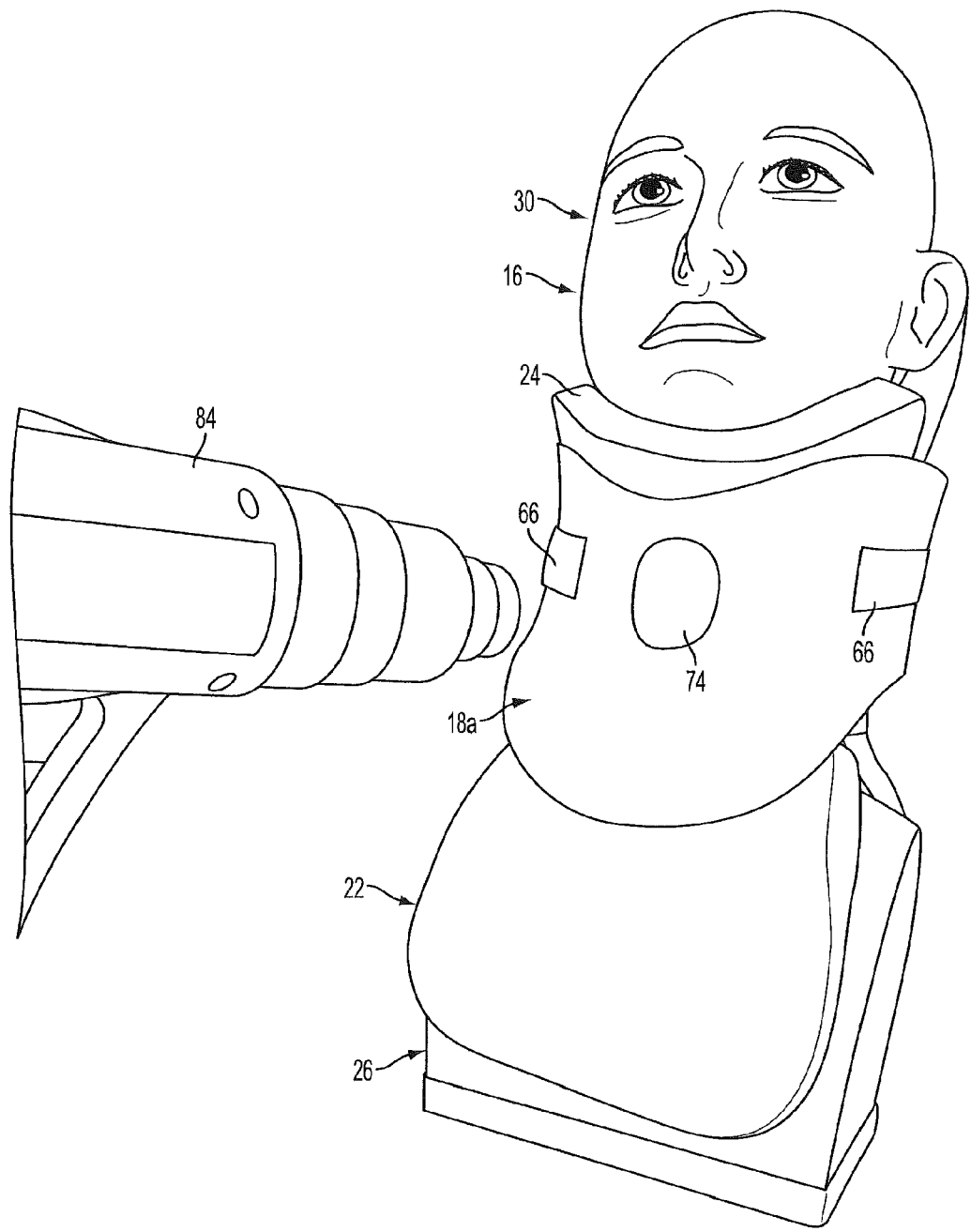
FIG. 9 is a perspective view of a heat gun heating the front blank.
Figure 10:
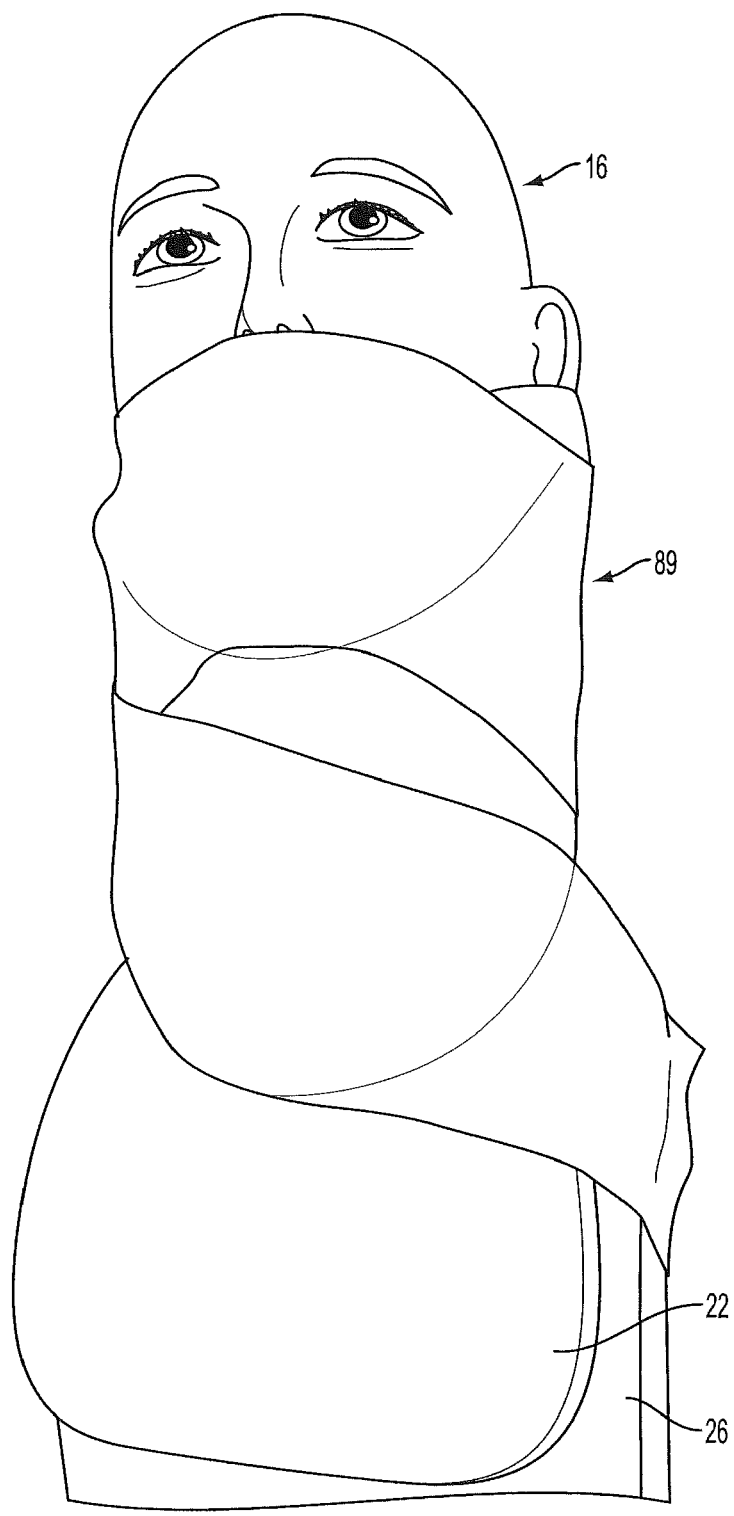
FIG. 10 is a perspective view of the front blank wrapped.

As shown in FIG. 9, the blanks 18a, 18b are then molded to the model 16. In the illustrated embodiment, the front blank 18a is positioned on the model 16 and a heating device, such as heat gun 84, heats the front blank 18a to mold it to the model 16. As shown in FIG. 10, after the blank is sufficiently heated (e.g., for 3-5 minutes) and reaches an appropriate temperature, the blank can be wrapped with, for example, an ace bandage 87 or other wrapping material to hold the front blank 18a to the model 16 to aid in retention of its formed shape while the blank 18a cools. Similar steps are repeated for the back blank 18b at the back of model 16.

Figure 11:
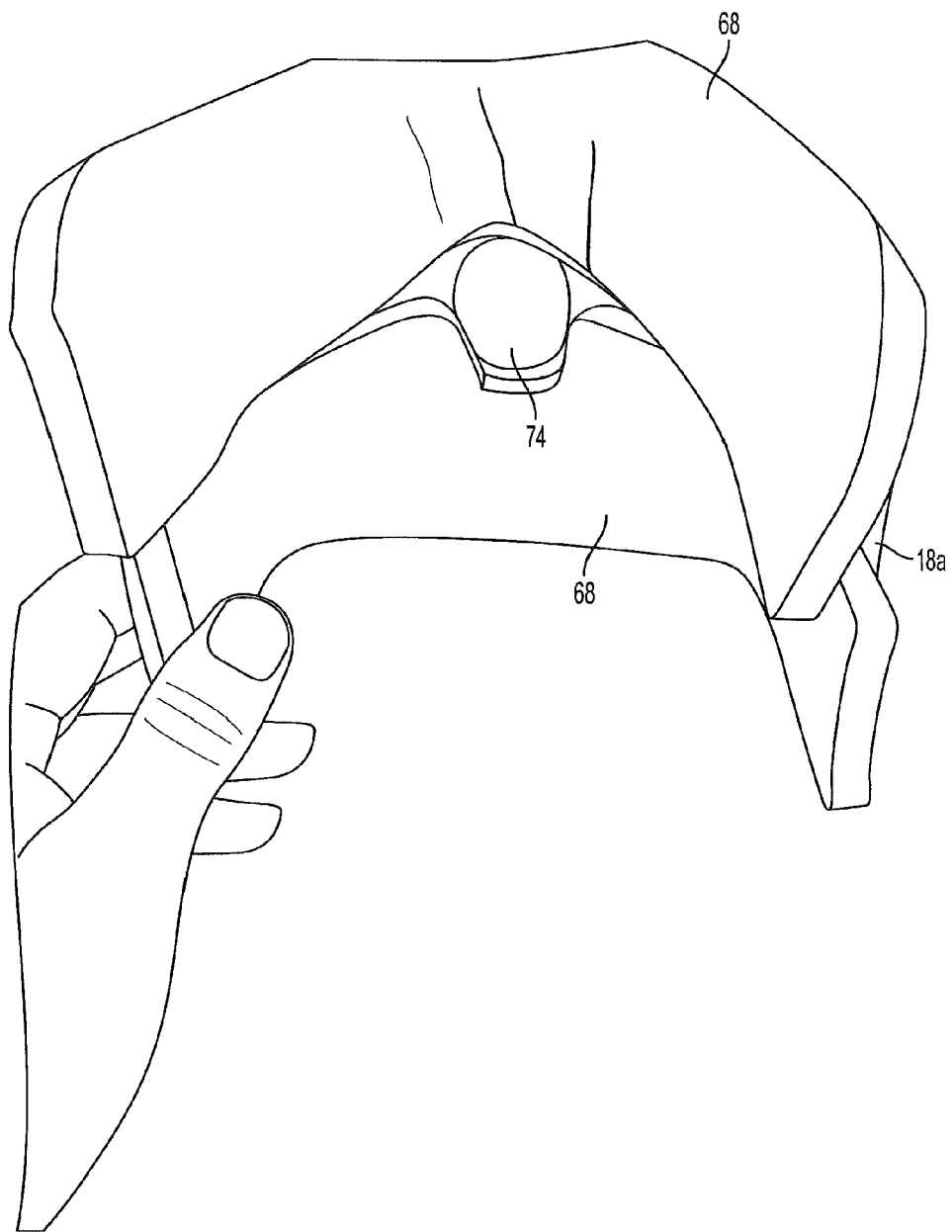
FIG. 11 is a perspective view of the interior of the front blank with padding.

Once the front and back blanks 18a, 18b have cooled, they are removed from the model 16. Although, the front and back blanks 18a, 18b are now molded to the specific size of the patient, trimming of the edges may be needed on a case by case basis to fit even closer to the patient. The molded front blank 18a is removed from the model. Next, as illustrated in FIG. 11, foam padding 68 may be added to the interior of the front blank 18a and the back blank 18b.

Next, a Velcro® strap 79 can be wrapped around the molded back blank 18b and secured to the Velcro® attachments 66 on the exterior of the molded front and back blanks 18a, 18b forming the custom molded collar 12, as illustrated in FIG. 12, sized to mimic the patient. The custom molded collar 12 is shown on a model 16 in FIG. 13.

Figure 15:
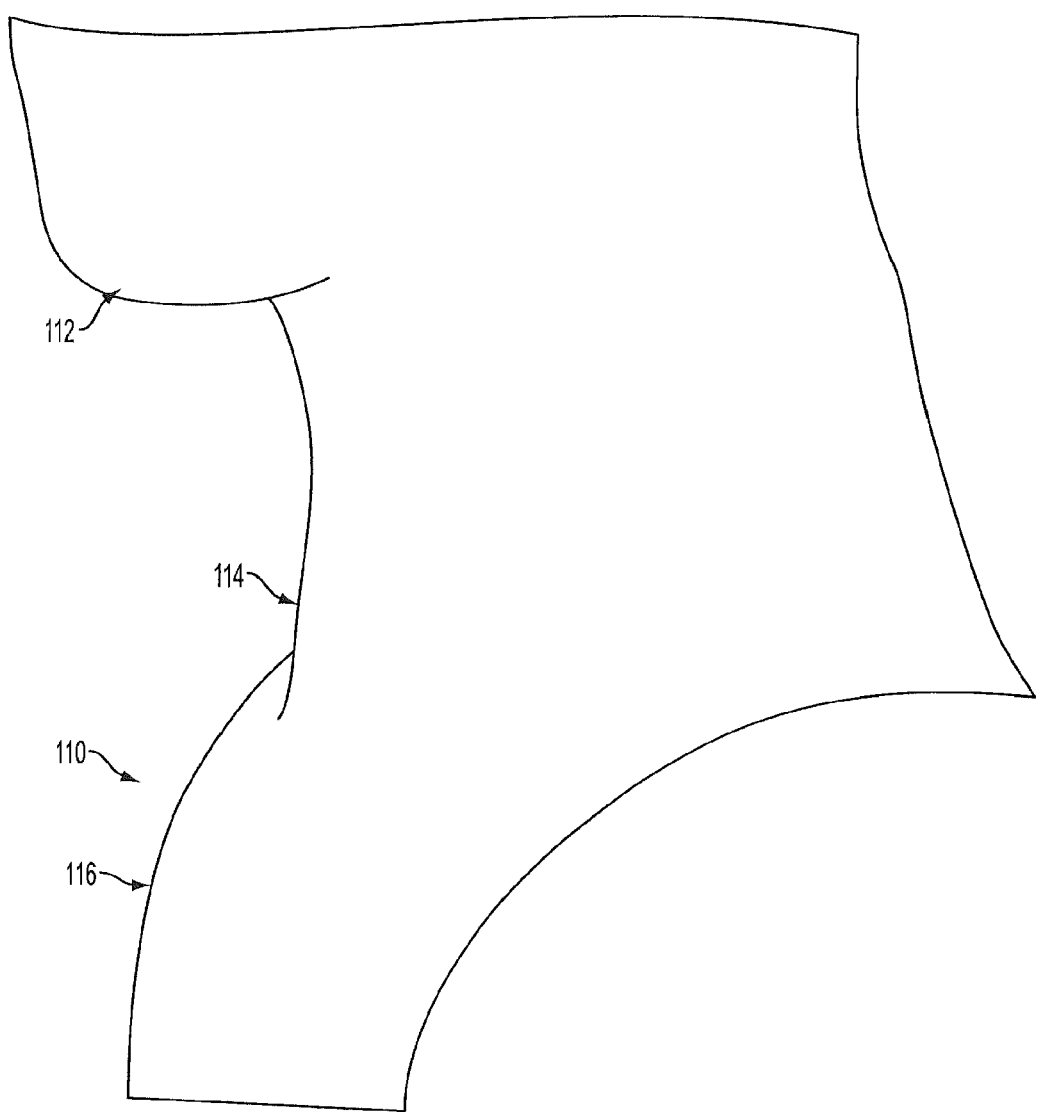
FIG. 15 is a side view of a mold for fabricating a front blank.
Figure 16:
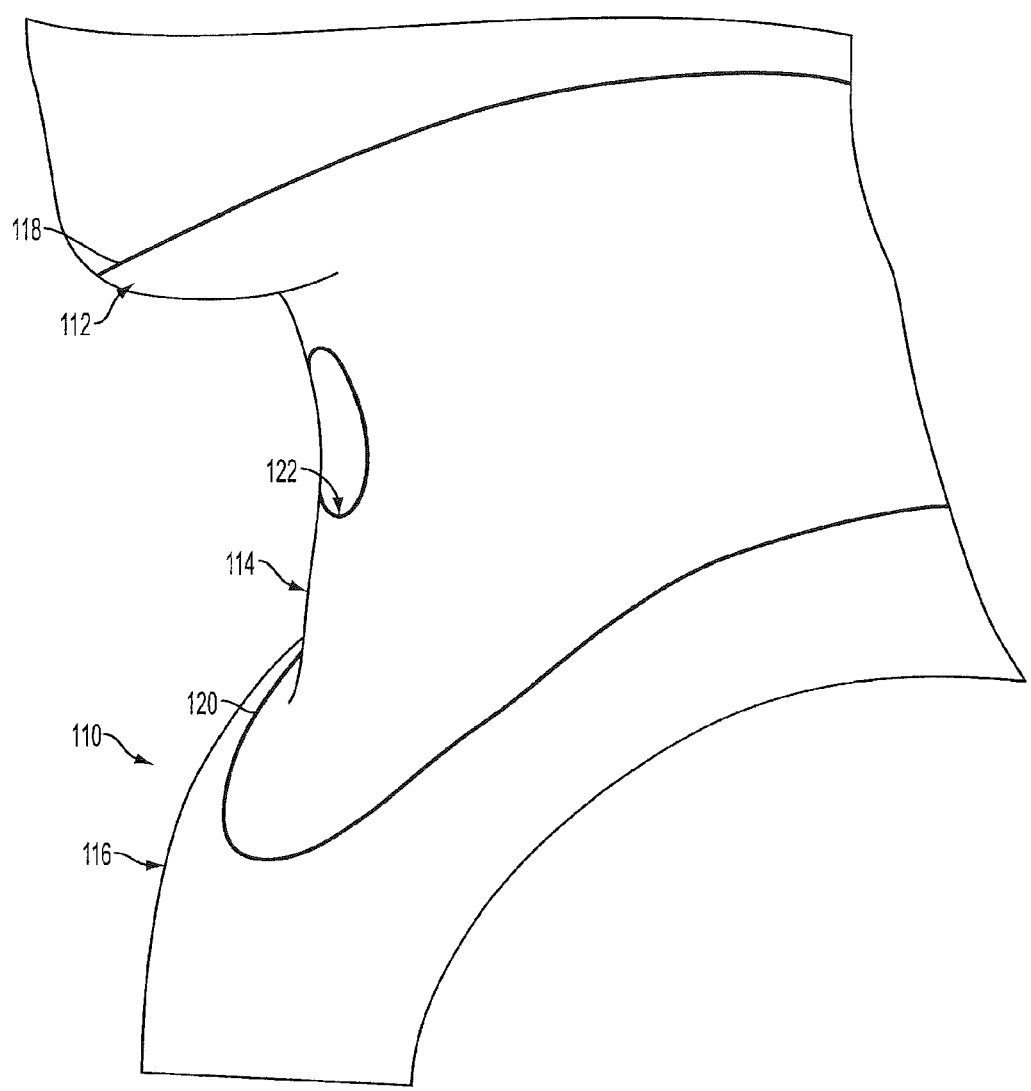
FIG. 16 is a side view of the mold of FIG. 15 with an outline provided thereon.
Figure 17:
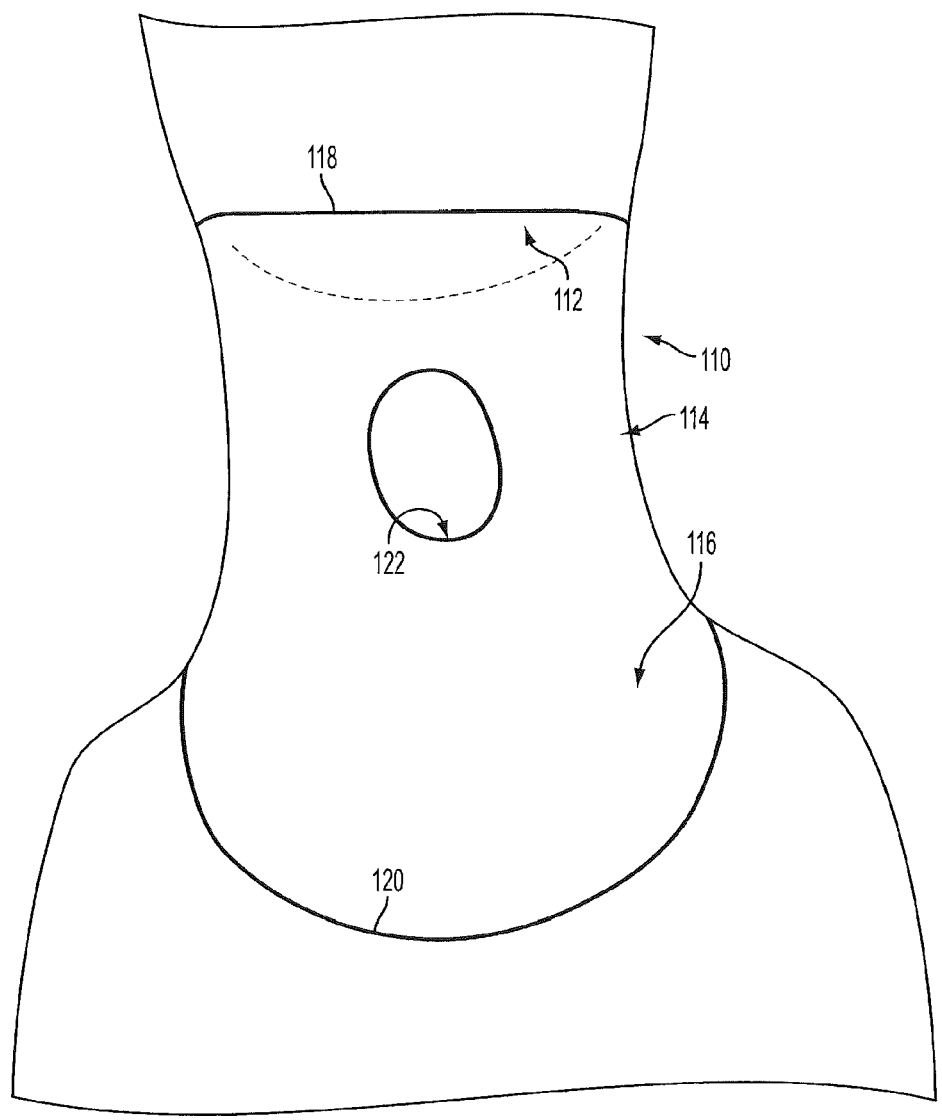
FIG. 17 is a front view of the mold of FIG. 15 with an outline provided thereon.

FIGS. 15-17 show a blank mold in the shape of the front of a human or humanoid, generally indicated at 110, sized and configured for creating a front blank 18a (see FIG. 23) which can be used to create a neck brace that is sized specifically for an individual patient or user. The blank mold 110 may be formed from plaster, wood, metal, or any other suitable material capable of withstanding heating.

As shown in FIG. 15, the blank mold 110 has a chin section 112, a neck section 114, and a chest section 116 each of which generally corresponds to the chin portion, neck portion, and upper chest portion of a human or humanoid shape. Optionally, as shown in FIGS. 16 and 17, an outline that corresponds to an outline of a front blank 18a may be drawn on the blank mold 110. The outline can include lines demarking an upper edge 118, a lower edge 120, and an opening 122. The outline may be utilized to trace the edges of the blank 18a, providing a path along which the blank 18a can be cut.

Figure 18:
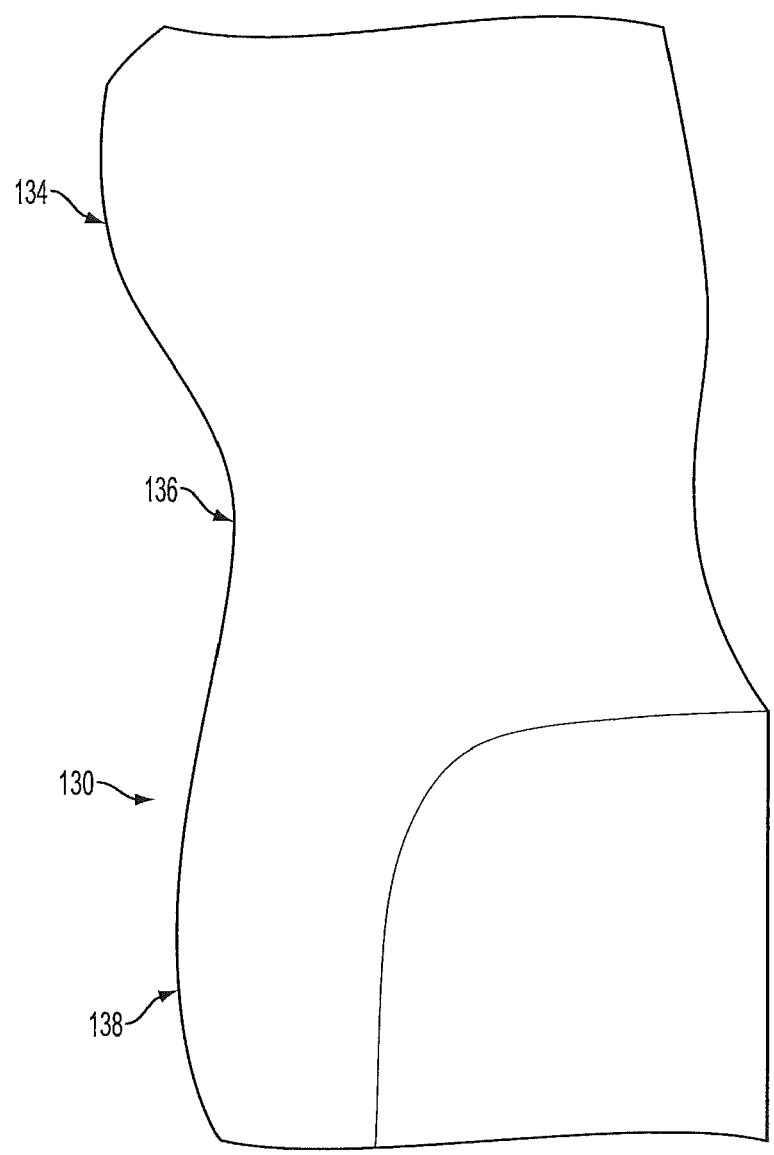
FIG. 18 is a side view of the mold for fabricating a back blank.
Figure 19:
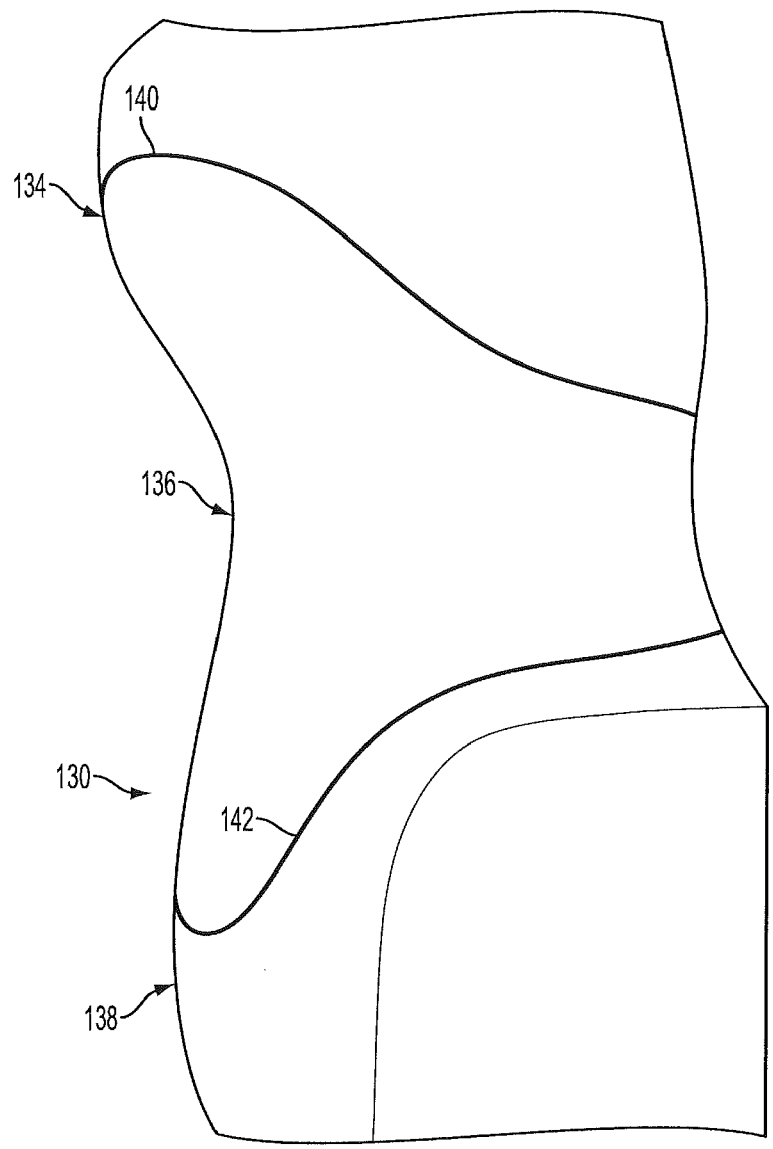
FIG. 19 is a side view of the mold of FIG. 18 with an outline provided thereon.
Figure 20:
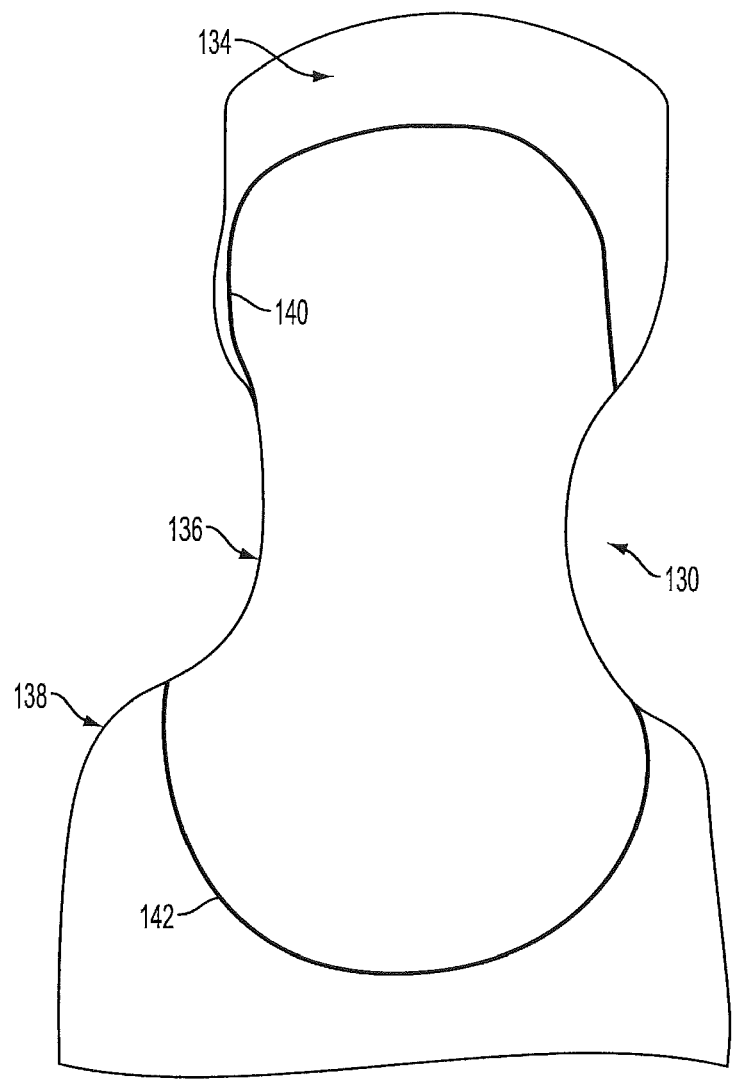
FIG. 20 is a back view of the mold of FIG. 18 with an outline provided thereon.
Figure 26:
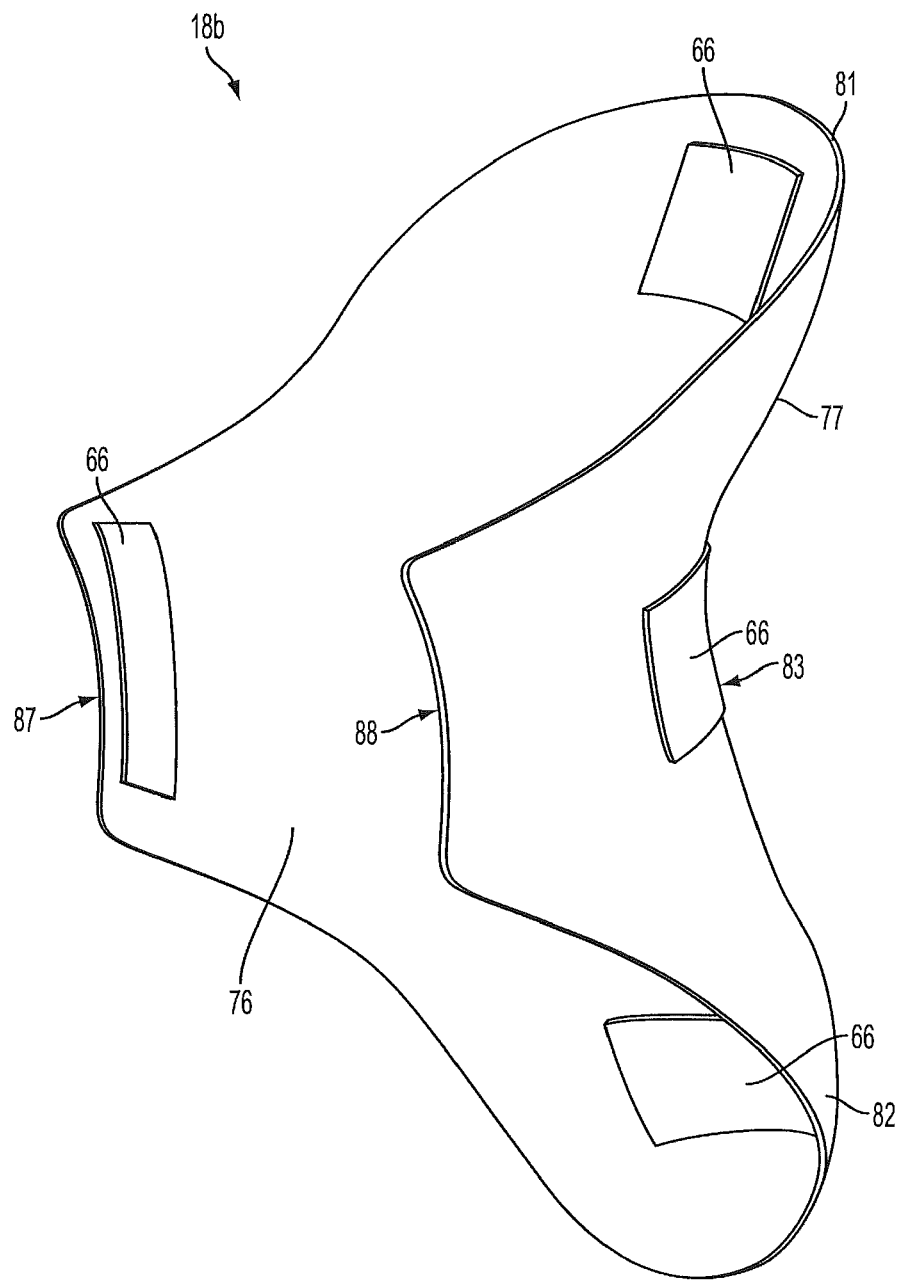
FIG. 26 is a perspective view of the back blank.

FIGS. 18-20 show a blank mold in the shape of the back of a human or humanoid shape, generally indicated at 130, for creating a back blank 18b (see FIG. 26). The blank mold 130 may be made from plaster, wood, metal, or any other suitable material capable of withstanding heating. As shown in FIG. 18, the blank mold 130 has a lower head section 134, a neck section 136, and a back section 138 each of which generally corresponds to the lower head portion, neck portion, and upper back portion of a human or humanoid shape. Optionally, an outline as shown in FIGS. 19 and 20, an outline that corresponds to an outline of a back blank 18b may be drawn on the blank mold 130. The outline can include lines demarking an upper edge 140 and a lower edge 142. The outline may be utilized to trace the edges of the blank 18b, providing a path along which the blank 18b can be cut.

Blank molds 110, 130 typically are formed from standard casting techniques, with plaster or other material capable of being cast poured into a form or shape of a mold, then allowing the plaster or other material to solidify to create the front and back blank molds 110, 130. Other techniques may be used to form the blank mold(s) without departing from the spirit of the disclosure, such as wood, metal, or composition. Optionally, blank molds 110, 130 may be obtained preformed with blanks 18a and 18b being formed thereon as detailed below without departing from the disclosure.

Figure 21:
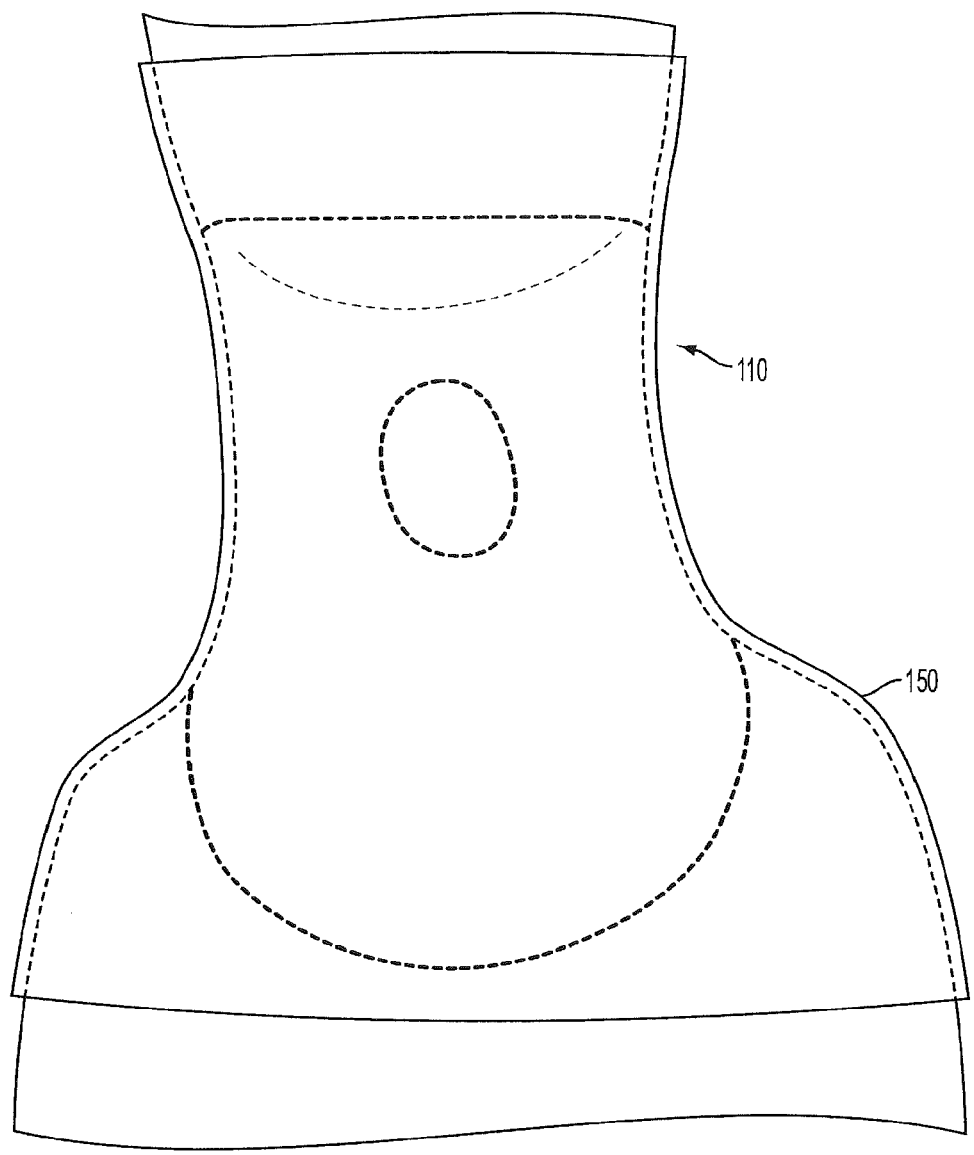
FIG. 21 is a view of the mold of FIG. 15 covered with a moldable material.
Figure 22:
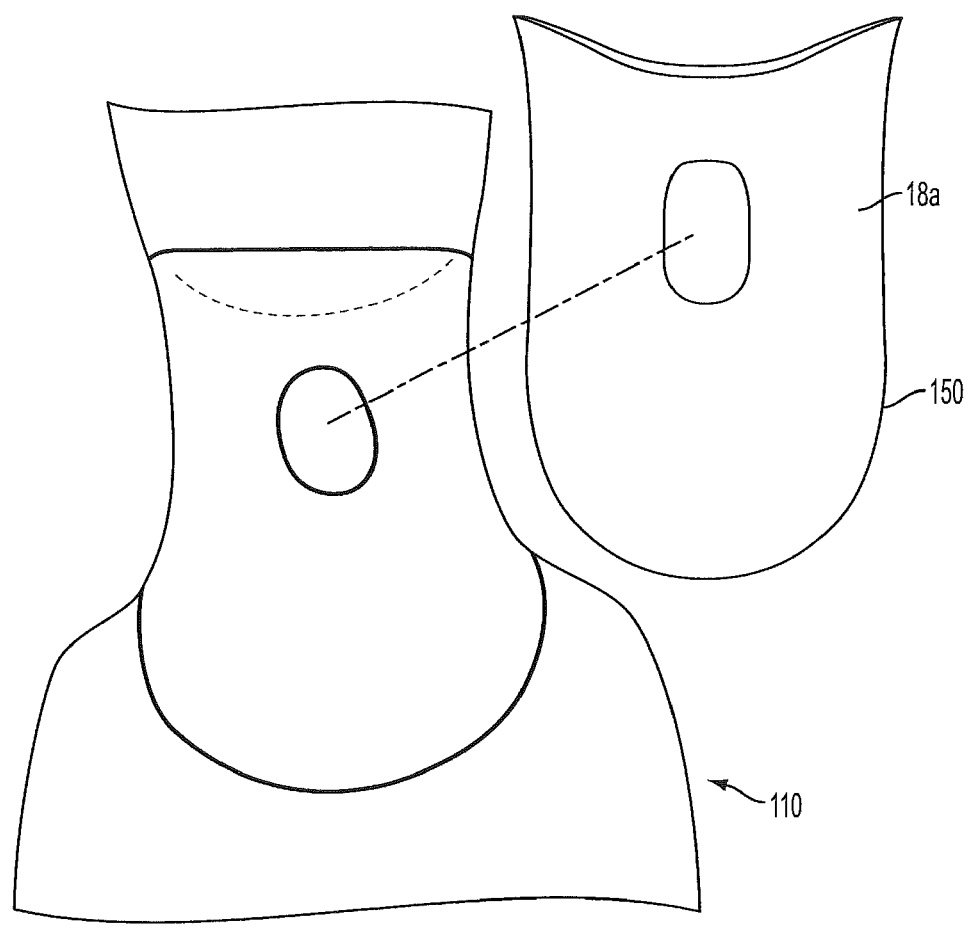
FIG. 22 is an exploded view of the mold of FIG. 15 and a front blank.
Figure 24:
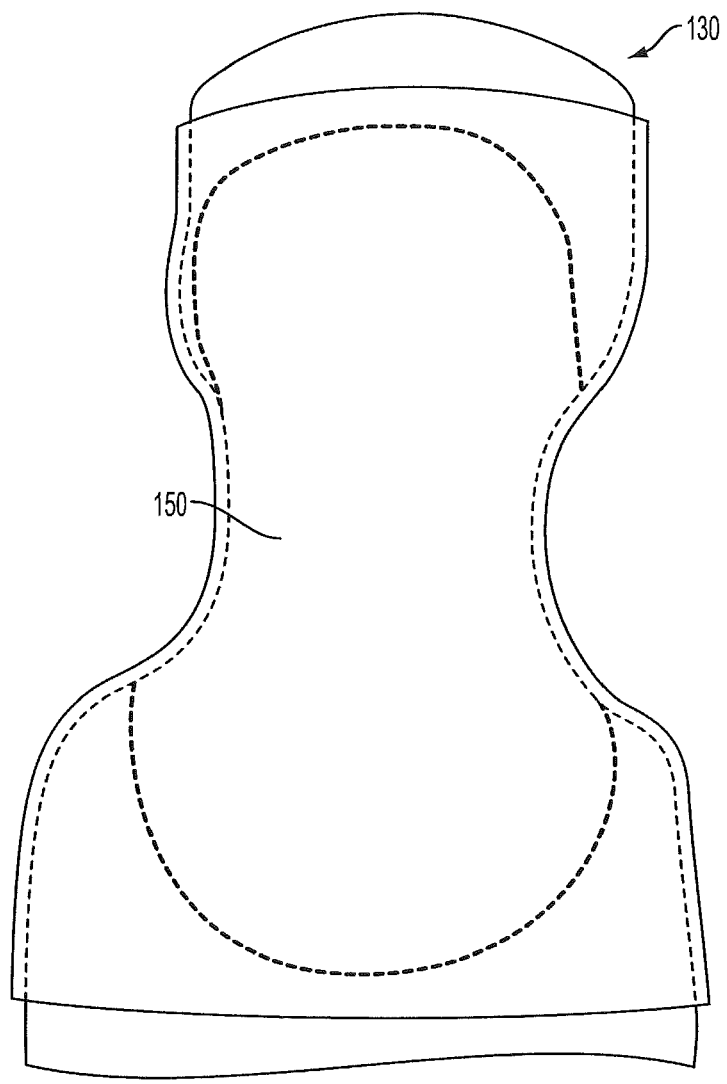
FIG. 24 is a view of the mold of FIG. 18 covered with a moldable material.
Figure 25:
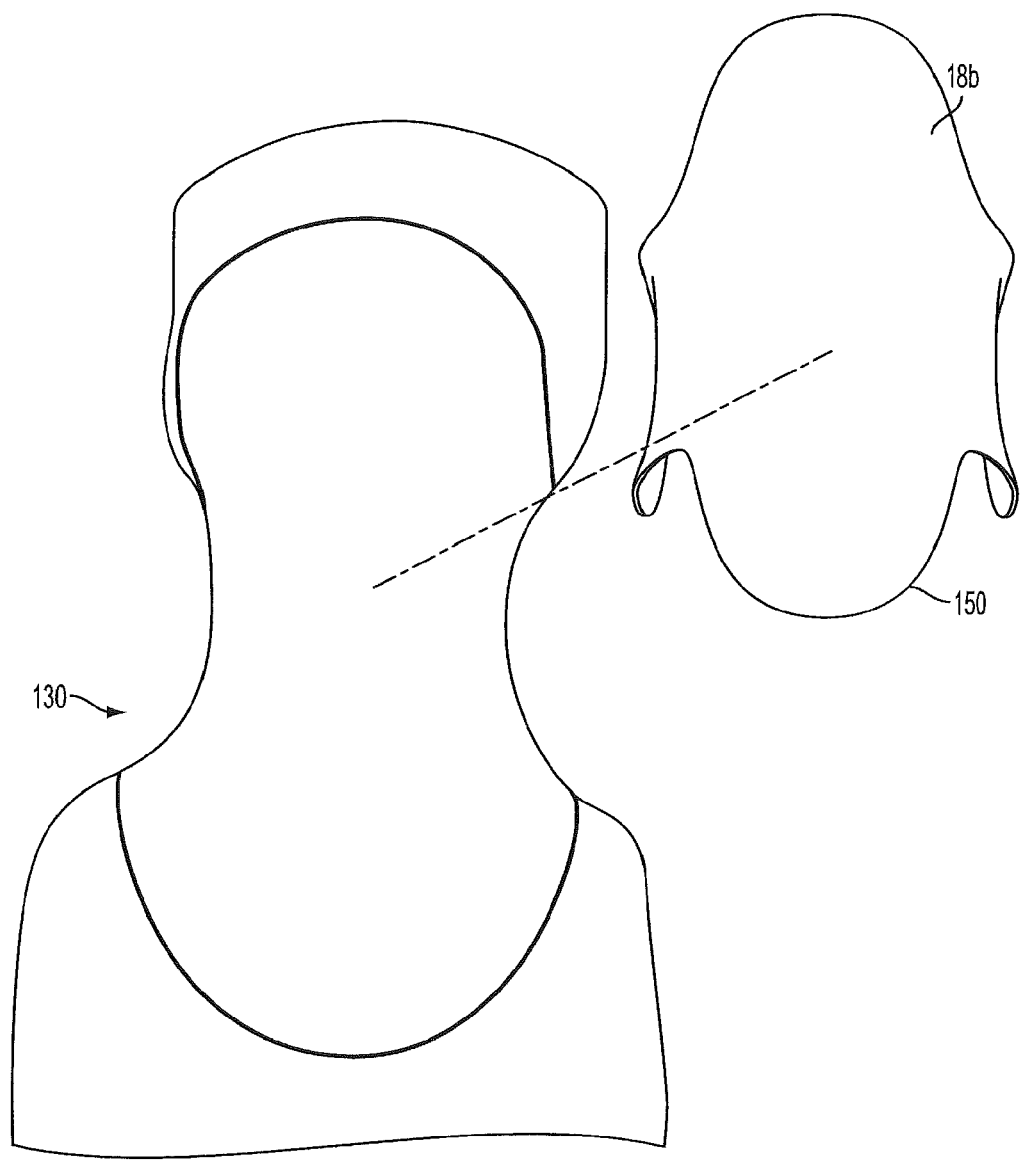
FIG. 25 is an exploded view of the mold of FIG. 18 and a back blank.

The molds shown in FIGS. 15-20 can be used to form front and back blanks conforming substantially to the profile or form of the front and back molds. FIGS. 21 and 22 show a front blank 18a being formed thereon, with the resulting blank 18a being shown in FIG. 23. FIGS. 24 and 25 show a back blank 18b being formed thereon, with the resulting blank 18b being shown in FIG. 26.

Figure 23:
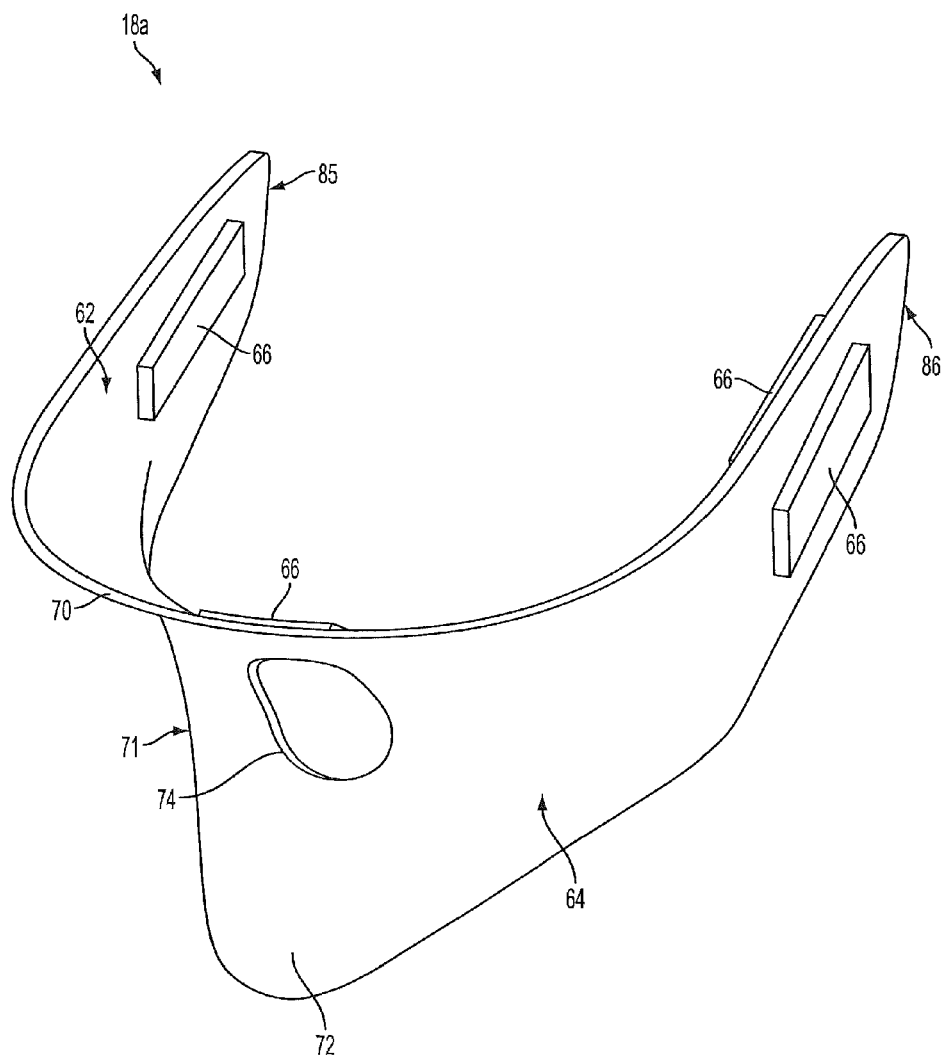
FIG. 23 is a perspective view of the front blank.

In order to form the front and/or back blank, as shown at FIG. 23 and FIG. 26, a sheet of moldable material 150 is placed over blank mold 110, 130. The material 150 is then vacuum formed or otherwise molded to the blank mold 110, 130 to reconfigure the shape of the sheet 150 to the shape of the respective mold 110, 130. The sheet 150 is allowed to cool and then a blank (18a or 18b) may be separated from the remainder of the sheet 150, such as by cutting. The sheet 150 may be cut with a laser, box cutter, knife, scissors, or any other means capable of cutting through the sheet. As shown in the exemplary embodiments shown in the figures, the sheet 150 may be cut along the outline(s) (118, 120, 122, 140, 142) to from the front or back blanks 18a, 18b (specifically shown in FIGS. 22 and 25). Alternatively, the sheets 150 may be cut on the mold 110, 130 without following an outline and then removed from the mold 110, 130 without departing from the disclosure. Optionally, if desired to improve the finish, look, texture, or surface, the blanks can be buffed, e.g. with buffing equipment. Other ways of forming a blank from moldable material, including three dimensional scanners, plotters, or printers, injection molding, drape molding, or CAD/CAM are contemplated as being within the spirit and scope of the present invention.

As shown in detail in FIG. 23, front blank 18a formed from mold 110 has an interior 62 and an exterior 64 and is shown in figures having complementary, substantially concave configurations, namely an interior concave configuration and an exterior concave configuration. The exterior 64 of the front blank 18a includes a top area 70 generally formed at or along the chin profile of the blank mold 110, a central or middle area 71 generally formed at or along the neck profile of the blank mold 110, and a lower area 72 generally formed at or along the chest profile of the blank mold 110. The exterior 64 has a general concave configuration at the middle area 71 between the top area 70 and the lower area 72. The front blank 18a can include a hole or aperture 74 in the middle area 71 for, a ventilator connection or laryngeal prominence (Adam's apple) to extend therethrough, optionally. The middle area 71 of the interior 62 has ends 85, 86 and a generally U-shape, parabolic, or concave configuration between the ends 85 and 86.

As shown in detail in FIG. 26, the back blank 18b formed from the mold 130 includes an interior 76 and exterior 77 having a double concave configuration with an interior concave configuration and an exterior concave configuration. The exterior 77 of the back blank 18b includes a top area 81 generally formed to correspond to an occipital curvature of a head portion of the blank mold 130, a middle area 83 generally formed to correspond to a neck portion of the blank mold 130, and a lower portion 82 generally formed to correspond to a lower portion of the neck and upper portion of the back of the blank mold 130. The exterior 77 has a general concave configuration at the middle area 83 between the top area 81 and the lower portion 82. The middle area 83 of the interior 76 has ends 87, 88 and a generally U-shape, parabolic, or concave configuration between the ends 87 and 88. However, the blanks 18a, 18b may have other shapes such as flat without departing from the disclosure.

Figure 27:
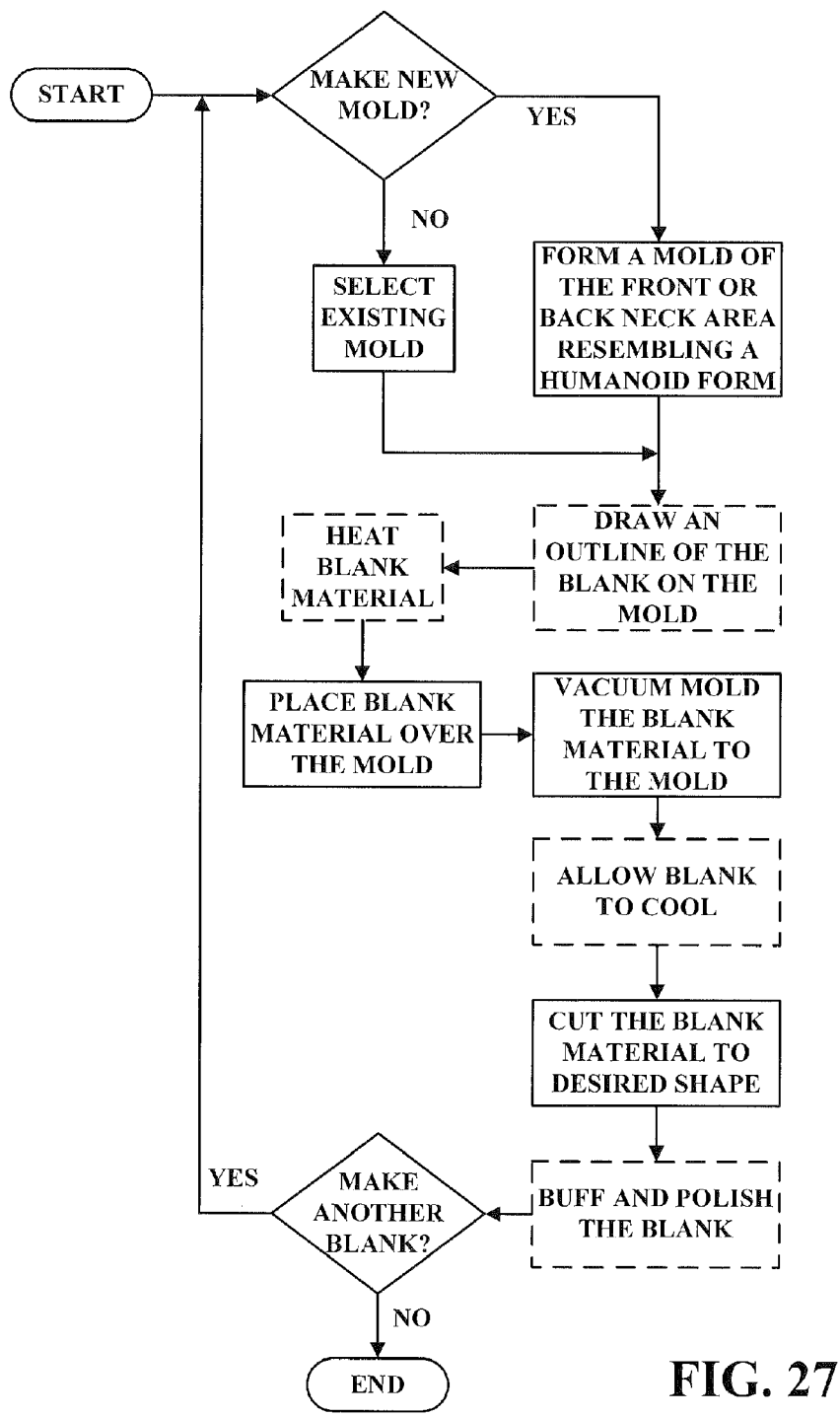
FIG. 27 is a flow chart of one exemplary method of forming a front blank and a back blank.

FIG. 27 shows a flow diagram of an exemplary process of forming front and back blanks. First, a decision step inquires whether a new mold is to be formed. If not, the process proceeds to selection of an existing front or back mold. If a new mold is to be formed, either a front or back mold is formed by casting the front or back mold in the form of a humanoid shape as detailed above. The process proceeds to an optional step where an outline of either a front blank or back blank is drawn on a respective front or back mold. Next, a blank material is selected and placed over the front or back mold. Optionally, the blank material can be preheated or otherwise warmed prior to being disposed over the front or back mold. The process then proceeds to a step where the blank material is molded to the mold. The blank material is generally then allowed to cool, if necessary. The molding can be by vacuum molding, heating, or otherwise to change an initial shape or profile of the blank material to a shape substantially corresponding to the form of the front or back mold, respectively. Other ways of forming a blank from moldable material, including three dimensional scanners, plotters, or printers, injection molding, drape molding, or CAD/CAM are contemplated as being within the spirit and scope of the present invention. Next, if the blank is larger than the desired size, the blank material can be separated into at least two sections to arrive at a desired shape of a front or back blank. The separating of the formed blank material is generally performed by cutting, such as with a knife or other sharp implement, or can be performed with a laser or other advanced cutting tool. The at least two sections include a front or back blank (such as the front blank shown in FIG. 23 or the back blank shown in FIG. 26) and a remainder portion. The remainder portion is generally discarded or collected for reuse, such as by reforming remainder portion(s) to use in additional blank material. Optionally, the process proceeds to a step where the blank is buffed or polished, e.g. to eliminate burrs, imperfections, or otherwise to clean up the front or back blank. If another blank is to be formed, the process shown in FIG. 27 returns to the decision step to inquire whether a new mold is to be formed. If another blank is not desired, the process ends.

The blanks 18a and 18b may be made from any suitable material, e.g. a low density polyethylene (LDPE), which is malleable and able to conform to at least a portion of either mold 110 or 130. In one exemplary embodiment, the material 150 may be a 24-inch×12-inch sheet of 3/32-inch thick LDPE. In order to form the sheet 150 to the shape of the front or back mold 110, 130, the material 150 can be heated (e.g. for about 330° F. for 5-6 minutes) inside an oven to become pliable or malleable. The dimensions and thickness of the material may be greater or lesser without departing from the disclosure. Further, other materials and methods of producing blanks can be used to form a blank without departing from the spirit of the disclosure.

The foregoing description generally illustrates and describes various embodiments of the present invention. It will, however, be understood by those skilled in the art that various changes and modifications can be made to the above-discussed construction of the present invention without departing from the spirit and scope of the invention as disclosed herein, and that it is intended that all matter contained in the above description or shown in the accompanying drawings shall be interpreted as being illustrative, and not to be taken in a limiting sense. Furthermore, the scope of the present disclosure shall be construed to cover various modifications, combinations, additions, alterations, etc., above and to the above-described embodiments, which shall be considered to be within the scope of the present invention. Accordingly, various features and characteristics of the present invention as discussed herein may be selectively interchanged and applied to other illustrated and non-illustrated embodiments of the invention, and numerous variations, modifications, and additions further can be made thereto without departing from the spirit and scope of the present invention as set forth in the appended claims.

What is claimed is:

1. A kit for making a custom configured neck brace, the kit comprising:
    a model having a selectively configurable neck portion;
    at least one blank having an initial configuration;
    the blank being formed of a material that is malleable when heated to a predetermined temperature;
    the initial configuration of the blank allowing the blank to be placed onto at least the neck portion of the model;
    the blank transformable to a final configuration different from the initial configuration when the blank is placed onto at least the neck portion of the model and heated, thereby forming at least a part of the custom configured neck brace.

2. The kit of claim 1 further comprises at least one wedge shaped neck block and at least one flexed rod to accommodate for uncorrectable flexion of the neck.

3. The kit of claim 1, wherein the selectively configurable neck portion is sized to mimic at least one measurement of a patient.

4. The kit of claim 3, wherein the final configuration of the blank generally corresponds to the at least one measurement of the patient.

5. A kit for making a custom configured neck brace, the kit comprising:
    a model having a selectively configurable neck portion;
    at least one blank having an initial configuration;
    the blank being formed of a material that is malleable when heated to a predetermined temperature;
    the initial configuration of the blank allowing the blank to be placed onto at least the neck portion of the model;
    the blank transformable to a final configuration different from the initial configuration when the blank is placed onto at least the neck portion of the model and heated, thereby forming at least a part of the custom configured neck brace;
    wherein the neck portion comprises neck blocks; the neck portion having a neck portion height and a neck portion width; the neck blocks including at least a first neck block having a first neck block height and a first neck block width.

6. The kit of claim 5 wherein the neck portion height can be increased by adding at least a second neck block of the neck blocks; the second neck block having a second neck block height and a second neck block width; wherein the first neck block width and the second neck block width are equal.

7. The kit of claim 6 wherein the second neck block height is different than the first neck block height.

8. The kit of claim 6 wherein the neck portion height can be increased by adding at least a third neck block of the neck blocks.

9. The kit of claim 8 wherein the neck portion height can be decreased by removing either the first neck block, the second neck block, or the third neck block.

10. The kit of claim 8 wherein the third neck block has a third neck block height and wherein the third neck block height is different than either the first neck block height, the second neck block height, or both the first neck block height and the second neck block height.

11. A kit for making a custom configured neck brace for a patient, the kit comprising:
at least one blank formed of a material that is malleable when heated to a predetermined temperature,
a model configured to mimic at least one measurement of the patient, the model comprises a selectively configurable neck portion, a head portion and an upper chest portion, the blank has an initial configuration allowing the blank to be placed onto at least a portion of the head portion, the neck portion, and the upper chest portion of the model, and the blank being transformable to a final configuration different from the initial configuration when the blank is placed onto at least the neck portion of the model and heated, the final configuration forms at least a part of the custom configured neck brace that generally corresponds to the at least one measurement of the patient.

12. The kit of claim 11 further comprising:
at least one chest base having a base portion, a front portion connected to the base portion, and a back portion connected to the base portion; each of the front portion and the back portion configured to increase the size of the upper chest portion of the model to mimic the patient.

13. The kit of claim 11 further comprising:
at least one chin and occipital base having a base portion, an occipital portion connected to the base portion, and a chin portion connected to the base portion; each of the occipital portion and the chin portion are configured to increase the size of a chin and occipital portion of the model to mimic the patient.

14. The kit of claim 11 wherein the head portion, the neck portion, and the upper chest portion are removably securely attached to one another by one of the following: one or more hook and loop fasteners, tongue and groove attachment, snaps, or at least one channel that extends from a top of the head portion through the neck portion and to a bottom of the upper chest portion, the at least one channel being configured to receive at least one rod to secure the head portion, neck portion, and upper chest portion together, wherein the at least one rod either corresponds to a number of channels or is less than the number of channels.

15. A method for making a custom configured neck brace, the method comprising the steps of:

obtaining a neck circumference and a chin to sternal notch distance of a user;
selecting neck blocks that correspond generally to the chin to sternal notch distance and to the neck circumference; the selected neck blocks forming a neck portion;
attaching the neck portion to a chin portion and an upper chest portion to create a model;
obtaining at least one blank having an initial configuration; the at least one blank being formed of a material that is malleable when heated to a predetermined temperature;
placing the at least one blank onto at least the neck portion of the model;
heating the at least one blank to at least the predetermined temperature;
allowing the at least one blank to transform to a final configuration different from the initial configuration;
allowing the at least one blank to cool in the final configuration; and
removing the at least one blank from the model.

16. The method of claim 15 wherein the head portion, the neck portion, and the upper chest portion are removably securely attached to one another by one of the following: one or more hook and loop fasteners, tongue and groove attachment, snaps, or at least one channel that extends from the top of the head portion through the neck portion and to the bottom of the upper chest portion, the at least one channel being configured to receive at least one rod to secure the head portion, neck portion, and upper chest portion together, wherein the at least one rod either corresponds to the number of channels or is less than the number of channels, and wherein the method further comprises:
securing the head portion, the neck portion, and the upper chest portion together to form the model.

17. The method of claim 15 wherein the obtaining the neck circumference and the chin to sternal notch distance comprises:
measuring the neck circumference and the chin to sternal notch distance of the user.

18. The method of claim 15 wherein the at least one rod is a flexed rod and the neck blocks are wedge shaped neck blocks.

19. The method of claim 15 further comprising:
after heating, wrapping the at least one blank with a wrap to hold the at least one blank in place against the model during cooling; and
after removing, applying padding to the final configuration.

20. A method of forming a neck brace from a blank, the method comprising:
placing the blank onto a model having at least a selectively configurable neck portion; the blank having an initial configuration;
heating the blank to transform the blank from the initial configuration to a molded configuration different from the initial configuration;
wherein the molded configuration conforms generally to at least a portion of the shape of the neck portion of the model when the blank is heated; the blank being transformed from the initial configuration to the molded configuration before being the blank is removed from the model.

21. The method of claim 20 wherein the blank further comprises an interior surface and an exterior surface; a central portion, an upper portion, and a lower portion; the upper portion and the lower portion extend outwardly from the central portion; the central portion of the interior surface defines a substantially parabolic shaped interior space; and the exterior surface having a generally concave shape.

22. The method of claim 20 wherein the material is a low density polyethylene.

23. The method of claim 20 wherein the blank comprises an aperture in the central portion.

24. A method for making a custom configured neck brace, the method comprising the steps of:
- obtaining a neck circumference and a chin to sternal notch distance of a user;
- sizing a neck portion of a model generally to correspond to the chin to sternal notch distance and to the neck circumference;
- attaching the neck portion to a chin portion and an upper chest portion to create the model;
- obtaining at least one blank having an initial configuration, the at least one blank being formed of a material that is malleable when heated to a predetermined temperature;
- placing the at least one blank onto the neck portion of the model;
- heating the at least one blank to at least the predetermined temperature; and
- transforming the at least one blank to a molded configuration different from the initial configuration.

25. The method of claim 24, further comprising:
- allowing the molded configuration of the at least one blank to cool;
- removing the molded configuration of the at least one blank from the model; and
- fitting the molded configuration onto the user.

26. The method of claim 25, wherein the fitting comprises cutting, buffing, or polishing to modify the molded configuration.

* * * * *